(12) United States Patent
Metzler et al.

(10) Patent No.: US 9,163,286 B2
(45) Date of Patent: Oct. 20, 2015

(54) DRY COMPOSITION OF REACTION COMPOUNDS WITH STABILIZED POLYMERASE

(71) Applicant: Roche Diagnostics Operations, Inc., Indianapolis, IN (US)

(72) Inventors: Thomas Metzler, Munich (DE); Tobias Haslinger, Sindelsdorf (DE); Annette Peceny, Wolfratshausen (DE); Harald Sobek, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 77 days.

(21) Appl. No.: 14/169,993

(22) Filed: Jan. 31, 2014

(65) Prior Publication Data
US 2014/0162267 A1   Jun. 12, 2014

Related U.S. Application Data

(62) Division of application No. 12/641,747, filed on Dec. 18, 2009, now Pat. No. 8,652,811.

(30) Foreign Application Priority Data

Dec. 19, 2008   (EP) .................... 08022082

(51) Int. Cl.
*C12P 19/34*   (2006.01)
*C12Q 1/68*    (2006.01)
*C12N 9/12*    (2006.01)

(52) U.S. Cl.
CPC ............ *C12Q 1/6876* (2013.01); *C12N 9/1252* (2013.01)

(58) Field of Classification Search
CPC ........................... C12N 9/1252; C12Q 1/6876
USPC ........................................... 435/91.2
See application file for complete search history.

(56) References Cited

U.S. PATENT DOCUMENTS

| | | |
|---|---|---|
| 3,300,474 A | 1/1967 | Flodin et al. |
| 5,098,893 A | 3/1992 | Franks et al. |
| 5,118,801 A | 6/1992 | Lizardi et al. |
| 5,200,399 A | 4/1993 | Wettlaufer et al. |
| 5,210,015 A | 5/1993 | Gelfand et al. |
| 5,240,843 A | 8/1993 | Gibson et al. |
| 5,270,163 A | 12/1993 | Gold et al. |
| 5,475,096 A | 12/1995 | Gold et al. |
| 5,487,972 A | 1/1996 | Gelfand et al. |
| 5,538,848 A | 7/1996 | Libak et al. |
| 5,565,318 A | 10/1996 | Walker et al. |
| 5,593,824 A | 1/1997 | Treml et al. |
| 5,723,591 A | 3/1998 | Livak et al. |
| 5,804,375 A | 9/1998 | Gelfand et al. |

| | | |
|---|---|---|
| 7,407,747 B2 | 8/2008 | Perry et al. |
| 2004/0072167 A1 | 4/2004 | Perry et al. |
| 2007/0117094 A1 | 5/2007 | Hayashizaki et al. |

FOREIGN PATENT DOCUMENTS

| | | |
|---|---|---|
| EP | 1002875 A1 | 5/2000 |
| EP | 1674569 A1 | 6/2006 |
| WO | 9746707 A3 | 11/1997 |
| WO | 9746712 A2 | 11/1997 |
| WO | 9746714 A1 | 11/1997 |
| WO | 0137291 A1 | 5/2001 |
| WO | 03057910 A2 | 4/2003 |
| WO | 03057910 A3 | 7/2003 |
| WO | 2006131391 | 12/2006 |
| WO | 2007106579 A3 | 9/2007 |
| WO | 2008036544 A1 | 3/2008 |

OTHER PUBLICATIONS

Yakimovich et al, Biochemistry (Moscow), vol. 68, No. 2, 2003.*
Carpenter, J. et al. "Rational Design of Stable Lyophilized Protein Formulations: Some Practical Advice," Pharmaceutical Research 14:8 (1997) 969-975.
Passot, S. et al., "Effect of Product Temperature During Primary Drying on the Long-Term Stability of Lyophilized Proteins," Pharmaceutical Development and Technology 12 (2007) 543-553.
Schwegman, J. et al. "Practical Formulation and Process Development of Freeze-Dried Products," Pharmaceutical Development and Technology 10 (2005) 151-173.
Noma et al., Biotechnology Letter, vol. 28, pp. 939-944, 2006.
BS, Chang, et al, 1995, "Enzyme thermostabilization by bovine serum albumin and other proteins: evidence for hydrophobic interactions", Publication Types, MeSh Terms, Substances, 203.
Chen, Chi-Hong B. , et al., 2008, "Aptamer-based endocytosis of a lysosomal enzyme", The National Academy of Sciences of the USA, 105(41):15908-15913.
Jayasena D., Sumedha, 1999, "Aptamers: An Emerging Class of Molecules That Rival Antibodies in Diagnostics", Clinical Chemistry, 45(9):1628-1650.
Dr. Polifke, Tobias, et al., 2007, "Langzeit-Stabilisierung von Assay-Komponenten", Laborwelt, 8:35-40.
Shigdar, Sarah, et al., 2010, "Aptamer Therapeautics: The 21st Century's Magic Bullet of Nanomedicine", The Open Conference Proceedings Journal, 1:118-124.
Siegmund, V., et al., 2005, "Dry-Reagent-Based PCR as a Novel Tool for Laboratory Confirmation of Clinically Diagnosed Mycobacterium Ulcerans-Associated Disease in Areas in the Tropics Where M. Ulcerans is Endemic", Journal of Clinical Microbiology, 43(1):271-276.

(Continued)

*Primary Examiner* — Cynthia B Wilder
(74) *Attorney, Agent, or Firm* — Faegre Baker Daniels LLP

(57) ABSTRACT

The present invention provides methods to obtain dry compositions of reaction compounds that maintain the biological activity of the compounds upon re-solubilization after a certain storage time. Preferably, the dry composition comprises a polymerase, and the dry composition is usable for polymerase chain reaction (PCR) amplification after re-solubilization.

4 Claims, 14 Drawing Sheets

(56) References Cited

OTHER PUBLICATIONS

Siegmund, Vera, et al, 2007, "Dry Reagent-Based Polymerase Chain Reaction Compared with Other Laboratory Methods available for the Diagnosis of Buruli Ulcer Disease", Clinical Infections Diseases, 45:68-75.

Terpe, Kay, 2008, "PCR ist immer noch Voodoo Ploymerase-Kettenreaktion", Laborjournal.

Test Protocol of a drying experiment, 08, 2013, "Einsprechenden Nachgestellten Trocknungsexperiments".

Yakimovich O., Yu, et al, 2003, "Influence of DNA Aptamer Structure on the Specificity of Binding to Tag DNA Polymerase", Biochemistry, 68(2):228-235.

* cited by examiner

SEQUENCE LISTING

<160> NUMBER OF SEQ ID NOS: 10

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gtggcggcac catgtct                                                  17

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctggttaaaa agattggttg cga                                           23

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
cagctggacc tacgggagcg gg                                            22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggcttagtga atccttcgga g                                             21

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtttacccaa ctttgcagtc ca                                            22

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
tgtgccgttg ccggctcaaa tag                                           23

<210> SEQ ID NO 7
<211> LENGTH: 3227
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 7

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctggc ttaactatgc ggcatcagag cagattgtac tgagagtgc      180
accatagatc ctgaggatcg gggtgataaa tcagtctgcg ccacatcggg ggaaacaaaa     240
tggcgcgaga tctaaaaaaa aaggctccaa aaggagcctt tcgcgctacc aggtaacgcg     300
ccactccgac gggattaacg agtgccgtaa cgacgatgg ttttaccgtg tgcggagatc      360
aggttctgat cctcgagcat cttaagaatt cgtcccacgg tttgtctaga gcagccgaca     420
atctgggtgg cggcaccatg tctggtcctc gagcgtatgg ggctttgtca cccgctcccg     480
taggtccagc tggcagctag cctcgcaacc aatctttta accagccaat ttcctgacgg      540
gtaattttga tttgcatgcc gtccgggtga gtcatagcgt ctggttgttt tgccagattc     600
agcagagtct gtgcaatgcg gccgctgacg tcgaggaacg ccaggttgcc cactttctca     660
ctagtgacct gcagccggcg cgccatctgt gcagacaaac gcatcaggat atccggattt     720
acctgaatca attggcgaaa ttttttgtac gaaatttcag ccacttcaca ggcggttttc     780
gcacgtaccc atgcgctacg ttcctggccc tcttcaaaca ggcccagttc gccaataaaa     840
tcaccctgat tcagatagga gaggatcatt tctttaccct cttcgtcttt gatcagcact     900
gccacagagc ctttaacgat gtagtacagc gtttccgctt tttcaccctg gtgaataagc     960
gtgctcttgg atgggtactt atgaatgtgg caatgagaca agaaccattc gagagtagga    1020
tccgtttgag gtttaccaag taccataaga tccttaaatt tttattatct agctagatga    1080
taatattata tcaagaattg tacctgaaag caaataaatt ttttatctgg cttaactatg    1140
cggcatcaga gcagattgta ctgagagtgc accatatgcg gtgtgaaata ccgcacagat    1200
gcgtaaggag aaaataccgc atcaggcgct cttccgcttc ctcgctcact gactcgctgc    1260
gctcggtcgt tcggctgcgg cgagcggtat cagctcactc aaaggcggta atacggttat    1320
ccacagaatc aggggataac gcaggaaaga acatgtgagc aaaaggccag caaaaggcca    1380
ggaaccgtaa aaaggccgcg ttgctggcgt ttttccatag gctccgcccc cctgacgagc    1440
atcacaaaaa tcgacgctca agtcagaggt ggcgaaaccc gacaggacta taaagatacc    1500
aggcgtttcc ccctggaagc tccctcgtgc gctctcctgt tccgaccctg ccgcttaccg    1560
gatacctgtc cgcctttctc ccttcgggaa gcgtggcgct ttctcatagc tcacgctgta    1620
ggtatctcag ttcggtgtag gtcgttcgct ccaagctggg ctgtgtgcac gaaccccccg    1680
ttcagcccga ccgctgcgcc ttatccggta actatcgtct tgagtccaac ccggtaagac    1740
acgacttatc gccactggca gcagccactg gtaacaggat tagcagagcg aggtatgtag    1800
gcggtgctac agagttcttg aagtggtggc ctaactacgg ctacactaga aggacagtat    1860
ttggtatctg cgctctgctg aagccagtta ccttcggaaa aagagttggt agctcttgat    1920
ccggcaaaca aaccaccgct ggtagcggtg gtttttttgt ttgcaagcag cagattacgc    1980
gcagaaaaaa aggatctcaa gaagatcctt tgatcttttc tacggggtct gacgctcagt    2040
```

| | |
|---|---|
| ggaacgaaaa ctcacgttaa gggattttgg tcatgagatt atcaaaaagg atcttcacct | 2100 |
| agatccttt aaattaaaaa tgaagtttta aatcaatcta agtatatat gagtaaactt | 2160 |
| ggtctgacag ttaccaatgc ttaatcagtg aggcacctat ctcagcgatc tgtctatttc | 2220 |
| gttcatccat agttgcctga ctccccgtcg tgtagataac tacgatacgg gagggcttac | 2280 |
| catctggccc cagtgctgca atgataccgc gagacccacg ctcaccggct ccagatttat | 2340 |
| cagcaataaa ccagccagcc ggaagggccg agcgcagaag tggtcctgca acttatccg | 2400 |
| cctccatcca gtctattaat tgttgccggg aagctagagt aagtagttcg ccagttaata | 2460 |
| gtttgcgcaa cgttgttgcc attgctacag gcatcgtggt gtcacgctcg tcgtttggta | 2520 |
| tggcttcatt cagctccggt tcccaacgat caaggcgagt tacatgatcc cccatgttgt | 2580 |
| gcaaaaaagc ggttagctcc ttcggtcctc cgatcgttgt cagaagtaag ttggccgcag | 2640 |
| tgttatcact catggttatg gcagcactgc ataattctct tactgtcatg ccatccgtaa | 2700 |
| gatgcttttc tgtgactggt gagtactcaa ccaagtcatt ctgagaatag tgtatgcggc | 2760 |
| gaccgagttg ctcttgcccg gcgtcaatac gggataatac cgcgccacat agcagaactt | 2820 |
| taaaagtgct catcattgga aaacgttctt cggggcgaaa actctcaagg atcttaccgc | 2880 |
| tgttgagatc cagttcgatg taacccactc gtgcacccaa ctgatcttca gcatctttta | 2940 |
| ctttcaccag cgtttctggg tgagcaaaaa caggaaggca aaatgccgca aaaagggaa | 3000 |
| taagggcgac acggaaatgt tgaatactca tactcttcct ttttcaatat tattgaagca | 3060 |
| tttatcaggg ttattgtctc atgagcggat acatatttga atgtatttag aaaaataaac | 3120 |
| aaataggggt tccgcgcaca tttccccgaa aagtgccacc tgctaagaaa ccattattat | 3180 |
| catgacatta acctataaaa ataggcgtat cacgaggccc tttcgtc | 3227 |

<210> SEQ ID NO 8
<211> LENGTH: 3200
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatagatc ctgaggatcg gggtgataaa tcagtctgcg ccacatcggg ggaaacaaaa | 240 |
| tggcgcgaga tctaaaaaaa aaggctccaa aaggagcctt tcgcgctacc aggtaacgcg | 300 |
| ccactccgac gggattaacg agtgccgtaa acgacgatgg ttttaccgtg tgcggagatc | 360 |
| aggttctgat cctcgagcat cttaagaatt cgtcccacgg tttgtctaga gcagccgaca | 420 |
| atctgggttt acccaacttt gcagtccaaa tgtgccgttg ccggctcaaa tagaccactc | 480 |
| cgaaggattc actaagcccc aatttcctga cgggtaattt tgatttgcat gccgtccggg | 540 |
| tgagtcatag cgtctggttg ttttgccaga ttcagcagag tctgtgcaat gcggccgctg | 600 |
| acgtcgagga acgccaggtt gcccactttc tcactagtga cctgcagccg gcgcgccatc | 660 |
| tgtgcagaca aacgcatcag gatatccgga tttacctgaa tcaattggcg aaatttttg | 720 |
| tacgaaattt cagccacttc acaggcggtt ttcgcacgta cccatgcgct acgttcctgg | 780 |
| ccctcttcaa acaggcccag ttcgccaata aaatcaccct gattcagata ggagaggatc | 840 |

| | |
|---|---|
| atttctttac cctcttcgtc tttgatcagc actgccacag agcctttaac gatgtagtac | 900 |
| agcgtttccg cttttcacc ctggtgaata agcgtgctct tggatgggta cttatgaatg | 960 |
| tggcaatgag acaagaacca ttcgagagta ggatccgttt gaggtttacc aagtaccata | 1020 |
| agatccttaa attttatta tctagctaga tgataatatt atatcaagaa ttgtacctga | 1080 |
| aagcaaataa attttttatc tggcttaact atgcggcatc agagcagatt gtactgagag | 1140 |
| tgcaccatat gcggtgtgaa ataccgcaca gatgcgtaag gagaaaatac cgcatcaggc | 1200 |
| gctcttccgc ttcctcgctc actgactcgc tgcgctcggt cgttcggctg cggcgagcgg | 1260 |
| tatcagctca ctcaaaggcg gtaatacggt tatccacaga atcaggggat aacgcaggaa | 1320 |
| agaacatgtg agcaaaaggc cagcaaaagg ccaggaaccg taaaaaggcc gcgttgctgg | 1380 |
| cgttttccca taggctccgc cccctgacg agcatcacaa aaatcgacgc tcaagtcaga | 1440 |
| ggtggcgaaa cccgacagga ctataaagat accaggcgtt tcccctgga agctccctcg | 1500 |
| tgcgctctcc tgttccgacc ctgccgctta ccggatacct gtccgccttt ctcccttcgg | 1560 |
| gaagcgtggc gctttctcat agctcacgct gtaggtatct cagttcggtg taggtcgttc | 1620 |
| gctccaagct gggctgtgtg cacgaacccc ccgttcagcc cgaccgctgc gccttatccg | 1680 |
| gtaactatcg tcttgagtcc aacccggtaa gacacgactt atcgccactg gcagcagcca | 1740 |
| ctggtaacag gattagcaga gcgaggtatg taggcggtgc tacagagttc ttgaagtggt | 1800 |
| ggcctaacta cggctacact agaaggacag tatttggtat ctgcgctctg ctgaagccag | 1860 |
| ttaccttcgg aaaagagtt ggtagctctt gatccggcaa acaaaccacc gctggtagcg | 1920 |
| gtggttttt tgtttgcaag cagcagatta cgcgcagaaa aaaaggatct caagaagatc | 1980 |
| ctttgatctt ttctacgggg tctgacgctc agtggaacga aaactcacgt taagggattt | 2040 |
| tggtcatgag attatcaaaa aggatcttca cctagatcct tttaaattaa aaatgaagtt | 2100 |
| ttaaatcaat ctaaagtata tatgagtaaa cttggtctga cagttaccaa tgcttaatca | 2160 |
| gtgaggcacc tatctcagcg atctgtctat ttcgttcatc catagttgcc tgactccccg | 2220 |
| tcgtgtagat aactacgata cgggagggct taccatctgg ccccagtgct gcaatgatac | 2280 |
| cgcgagaccc acgctcaccg gctccagatt tatcagcaat aaaccagcca gccggaaggg | 2340 |
| ccgagcgcag aagtggtcct gcaactttat ccgcctccat ccagtctatt aattgttgcc | 2400 |
| gggaagctag agtaagtagt tcgccagtta atagtttgcg caacgttgtt gccattgcta | 2460 |
| caggcatcgt ggtgtcacgc tcgtcgtttg gtatggcttc attcagctcc ggttcccaac | 2520 |
| gatcaaggcg agttacatga tcccccatgt tgtgcaaaaa agcggttagc tccttcggtc | 2580 |
| ctccgatcgt tgtcagaagt aagttggccg cagtgttatc actcatggtt atggcagcac | 2640 |
| tgcataattc tcttactgtc atgccatccg taagatgctt ttctgtgact ggtgagtact | 2700 |
| caaccaagtc attctgagaa tagtgtatgc ggcgaccgag ttgctcttgc ccggcgtcaa | 2760 |
| tacgggataa taccgcgcca catagcagaa ctttaaaagt gctcatcatt ggaaaacgtt | 2820 |
| cttcggggcg aaaactctca aggatcttac cgctgttgag atccagttcg atgtaaccca | 2880 |
| ctcgtgcacc caactgatct tcagcatctt ttactttcac cagcgtttct gggtgagcaa | 2940 |
| aaacaggaag gcaaaatgcc gcaaaaaagg gaataagggc gacacggaaa tgttgaatac | 3000 |
| tcatactctt ccttttcaa tattattgaa gcatttatca gggttattgt ctcatgagcg | 3060 |
| gatacatatt tgaatgtatt tagaaaaata aacaaatagg ggttccgcgc acatttcccc | 3120 |
| gaaaagtgcc acctgctaag aaaccattat tatcatgaca ttaacctata aaaataggcg | 3180 |

```
tatcacgagg ccctttcgtc                                                     3200

<210> SEQ ID NO 9
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cgatcatctc agaacattct tagcgttttg ttcttgtgta tgatcg                          46

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gatcatctca gaacattctt agcgttttgt tcttgtgtat ga                              42
```

DRY COMPOSITION OF REACTION COMPOUNDS WITH STABILIZED POLYMERASE

SEQUENCE LISTING

The instant application contains a Sequence Listing which has been submitted via EFS-Web and is hereby incorporated by reference in its entirety. Said ASCII copy, created on Dec. 17, 2009, is named 25614US.txt, and is 10,888 bytes in size.

RELATED APPLICATIONS

This application is a Divisional Application of U.S. patent application Ser. No. 12/641,747, filed Dec. 18, 2009, which will issue as U.S. Pat. No. 8,652,811 and which claims priority to EP 08022082.5 filed Dec. 19, 2008, the complete disclosures of which are hereby expressly incorporated by reference.

FIELD OF THE INVENTION

The present invention belongs to the field of dry compositions for polymerase chain reaction amplification amplification.

BACKGROUND OF THE INVENTION

Few biological reaction compounds are stable in solubilized form for any length of time, this is especially true for storage at room temperature. Consequently, an enormous amount of studies was performed in the past to evaluate possibilities to enhance the storage capabilities of biological reaction compounds in dry form.

Based on the large amount of state of the art documents in the field of dried reaction compounds, the person skilled in the art will be confident that it will be essential to use at least one stabilizing additive in order to assure the biological activity of e.g. a polymerase, upon re-solubilization.

WO 2008/36544 describes the use of so-called filler materials in order to provide dried compositions, the filler materials are e.g. carbohydrates such as FICOLL, sucrose, glucose, trehalose, melezitose, DEXTRAN or mannitol, proteins such BSA, gelatin or collagen and polymers such as PEG or polyvinyl pyrrolidone (PVP). Glass-forming filler materials for stabilizing biological reagents are further described in U.S. Pat. Nos. 5,098,893, 5,200,399 and 5,240,843. The filler material FICOLL is a copolymer disclosed in U.S. Pat. No. 3,300,474.

Moreover, the methods of drying the liquid reaction mixtures are most of the time very complex in nature and therefore, the drying procedures are demanding and expensive. In literature, freeze-drying (U.S. Pat. No. 5,593,824) or vacuum drying (U.S. Pat. No. 5,565,318) is used for drying the biological materials in a carbohydrate polymer matrix. Lyophilization or freeze-drying is a well established technique towards storage of proteins that is disclosed in many state of the art documents (e.g. Passot, S., et al., Pharmaceutical Development and Technology 12 (2007) 543-553; Carpenter, J. F., et al., Pharmaceutical Research 14(8) (1997) 969-975; Schwegman, J. J., et al., Pharmaceutical Development and Technology 10 (2005) 151-173).

A selection of drying conditions for different reaction mixtures for sequencing applications comprising genetic modifications of the Taq polymerase are described in U.S. Pat. No. 7,407,747. Drying procedures used are freeze-drying, speedvac without additional heat, speedvac with additional heat and air drying at room temperature. The reaction mixtures within this patent were tested with respect to a variety of cryoprotectants such as trehalose, sucrose, glucose and trimethylamine-N-oxide (TMANO). Moreover, experiments were also performed without cryoprotectants at all, but no data was disclosed concerning the stability of those reaction mixtures with time. A good stability for as long as 8 weeks was reported only for reaction mixtures comprising trehalose and bovine serum albumin (BSA).

Moreover, U.S. Pat. No. 7,407,747 discloses experiments with the polymerase in different sequencing mixtures, the sequencing mixtures comprise different compositions of buffer solution, nucleotides, nucleotides with fluorescence label and primers. There is no disclosure, if a polymerase in mixtures for real-time PCR amplifications, namely mixtures comprising buffer solution, nucleotides, primers and detection probes, may be dried and stored without affecting the PCR activity of the polymerase.

The present invention provides a method to dry a Taq DNA polymerase within a real-time PCR mixture, whereas the obtained dry composition can be stored without affecting the PCR performance of the Taq DNA polymerase.

SUMMARY OF THE INVENTION

To provide a dry composition of reaction compounds comprising a polymerase is a complex problem, especially if it is intended to store the dried composition for a certain amount of time and the subsequent re-solubilization of the dried composition must be possible without effecting the polymerase activity for PCR applications.

During drying of a liquid solution comprising different components, the concentration of the components will increase continuously, such that the properties change drastically, whereas the exact behavior of the liquid solution will depend on the components and the drying procedure. The skilled person will appreciate e.g. that high salt concentrations will destabilize proteins and that buffers will alter their behavior at high concentration such that extreme pH values may occur.

As mentioned before, the person skilled in the art will know about certain compounds that can be added to solutions comprising a polymerase in order to enhance the stability of the polymerase upon drying. Moreover, the person skilled in the art will not expect to obtain the same drying result for a certain polymerase, if components of the polymerase mixture will be changed.

E.g., U.S. Pat. No. 7,407,747 discloses that a Taq polymerase can be dried in a mixture consisting of buffer solution, nucleotides, BSA and trehalose and the polymerase remained active for as long as 8 weeks.

Throughout the present invention methods were developed to provide a dry composition of a polymerase for PCR application, the composition not only comprises buffers and nucleotides, but additional components to form an entire detection mixture, namely primers or even primers and probes.

It was realized that a liquid mixture comprising a polymerase, nucleotides and a stabilizing molecule may be dried and stored without effecting the polymerase activity, whereas the polymerase activity was lost, if additionally primers were added to the liquid mixture. In more detail, due to the addition of primers, the PCR performance was already lost, if the re-solubilization occurred directly after the drying procedure.

This technical problem of increasing the stability of the Taq polymerase such that the liquid mixture to be dried may comprise additionally primers was solved by the present invention.

Surprisingly, it was found that the addition of an aptamer to the liquid solution enhanced the stability of the Taq polymerase, wherein the stabilization was good enough not only to dry, but also to store the dried mixture.

Consequently, one aspect of the present invention is a method to produce a storable dry composition of reaction compounds, the method comprising the steps
(a) providing a liquid mixture of reaction compounds, the liquid mixture comprises primers, nucleotides, a Taq DNA polymerase and a first stabilizing molecule, and
(b) drying the liquid mixture by reducing the pressure surrounding the liquid mixture,
wherein the dry composition of reaction compounds is soluble in aqueous solution, characterized in that the liquid mixture of reaction compounds in step a) further comprises an aptamer as a second stabilizing molecule.

Throughout the present invention the phrase "dry composition" is used to emphasize that the amount of solvent, preferably of aqueous solvents is reduced below 5 weight %.

The phrase "storable dry composition" implicates throughout the present invention that the dry composition must be storable for at least one week, preferably for at least 4 weeks, more preferably for more than 8 weeks, without affecting the polymerase activity.

A "stabilizing molecule" within the present invention is a molecule that improves the resistance of the polymerase against loss of its PCR activity upon drying an aqueous solution comprising the polymerase.

Another aspect of the present invention is a dry composition of reaction compounds comprising primers, nucleotides, a Taq DNA polymerase, a first stabilizing molecule and an aptamer as a second stabilizing molecule, the dry composition provides PCR activity upon re-solubilisation after storage at room temperature for at least one week.

Yet another aspect of the present invention is a method to perform a PCR amplification, the method comprises the steps
(a) re-solubilizing a dry composition of reaction compounds according to the present invention by addition of an aqueous solution, and
(b) performing a thermocycling protocol with the aqueous solution comprising the re-solubilized reaction compounds.

DETAILED DESCRIPTION OF THE INVENTION

Figure 1:
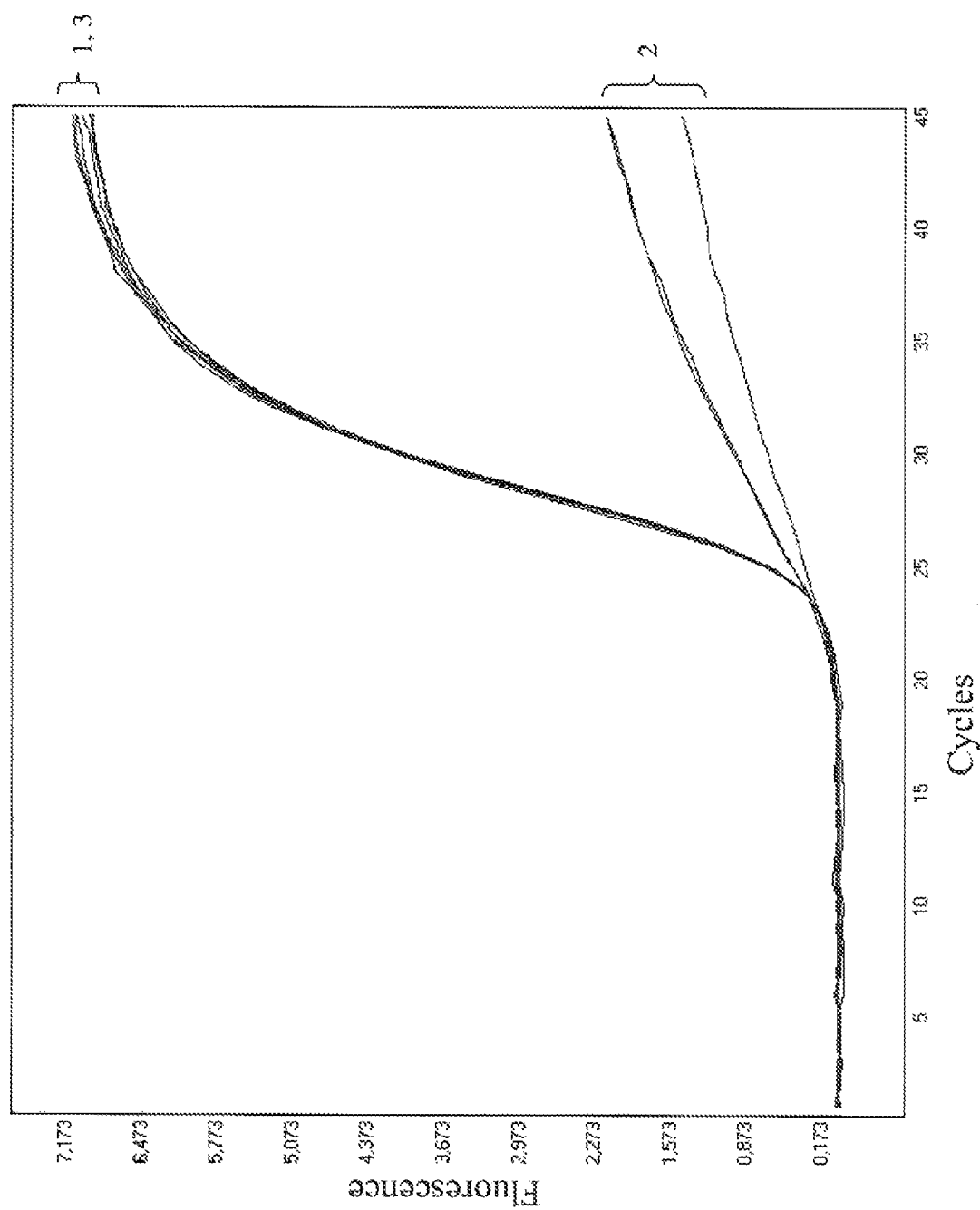
FIG. 1 Eamst Plasmid amplification with Taq polymerase and casein
FIG. 2 Wsebi Plasmid amplification with Taq polymerase and casein
FIG. 3 Eamst Plasmid amplification with Taq polymerase and BSA
FIG. 4 Wsebi Plasmid amplification with Taq polymerase and BSA
FIG. 5 Eamst Plasmid amplification with Taq polymerase, NTQ12-46A aptamer and casein
FIG. 6 Wsebi Plasmid amplification with Taq polymerase, NTQ12-46A aptamer and casein
FIG. 7 Eamst Plasmid amplification with Taq polymerase, NTQ12-46A aptamer and BSA
FIG. 8 Wsebi Plasmid amplification with Taq polymerase, NTQ12-46A aptamer and BSA
FIG. 9 Wsebi Plasmid amplification with Taq polymerase, NTQ12-46A aptamer and casein
FIG. 10 Wsebi Plasmid amplification with Taq polymerase, 21-41-P aptamer and casein
FIG. 11 Eamst Plasmid amplification with Taq polymerase, NTQ12-46A aptamer and casein
FIG. 12 Eamst Plasmid amplification with Taq polymerase, 21-41-P aptamer and casein
FIG. 13 Eamst Plasmid amplification with dried plasmid DNA, Taq polymerase, NTQ12-46A aptamer and casein
FIG. 14 Wsebi Plasmid amplification with dried plasmid DNA, Taq polymerase, NTQ12-46A aptamer and casein

One aspect of the present invention is a method to provide a storable dry composition of reaction compounds, the method comprising the steps
(a) providing a liquid mixture of reaction compounds, the liquid mixture comprises primers, nucleotides, a Taq DNA polymerase and a first stabilizing molecule, and
(b) drying the liquid mixture by reducing the pressure surrounding the liquid mixture,
wherein the dry composition of reaction compounds is soluble in aqueous solution, characterized in that the liquid mixture of reaction compounds in step a) further comprises an aptamer as a second stabilizing molecule.

Several groups of molecules are possible to choose a first stabilizing molecule for the Taq DNA polymerase from.

A preferred method according to the present invention is a method, wherein the first stabilizing molecule is a protein, preferably the stabilizing molecule is casein or BSA.

Another preferred method according to the present invention is a method, wherein the first stabilizing molecule is a carbohydrate, preferably the stabilizing molecule is trehalose or mannitol.

Yet another preferred method according to the present invention is a method, wherein the first stabilizing molecule is a synthetic polymer, preferably the stabilizing molecule is PEG or polyvinyl pyrrolidone (PVP).

It is the surprising finding of the present invention that another group of molecules can provide a stabilizing effect for the polymerase, namely the group of aptamers. Aptamers are known to bind to a polymerase in solution, whereas the so-called "hot start" feature is added to the polymerase (e.g. U.S. Pat. Nos. 5,475,096 and 5,270,163). In brief, the short oligonucleotides (aptamers) bind to the polymerase such that the polymerase activity is blocked. If the temperature is increased above a certain threshold during the thermocycling protocol of a PCR amplification, the aptamer will release the polymerase and the polymerase activity is initiated. Consequently, in "hot start" PCR the use of polymerase binding aptamers hinders the undesirable low temperature activity of polymerase until the reaction temperature is sufficient to exert high stringency for primer annealing.

As mentioned before, the Taq DNA polymerase within a mixture comprising buffer, nucleotides and a first stabilizing molecule could be dried, stored and re-solubilized without effecting the polymerase activity, but after adding primers to the mixture, the polymerase activity was lost directly after drying. Only after addition of an aptamer to the solution, the polymerase activity could be maintained again.

Without being bound to theory, it is expected that the hydroxyl group at the 3' end of the primers influences at least those amino acids of the polymerase that are responsible for the PCR activity. This theory was tested by additional experiments (data not shown), wherein the primers were replaced by phosphorylated primers and the PCR activity was analyzed after drying. It turned out that phosphorylated primers do not influence the polymerase and the liquid mixture of reaction compounds could be dried without the need for an additional aptamer.

In case of the Taq DNA polymerase, a mixture comprising buffer, nucleotides and e.g. casein as a stabilizing molecule could be dried, stored and re-solubilized without effecting the polymerase stability (see examples). After adding primers to the mixture, the PCR performance was lost directly after drying (data not shown, examples show only results after storage). Consequently, the requirements to stabilize the Taq polymerase for drying are increased due to the addition of primers to the liquid mixture.

Additional experiments showed that the aptamer without the first stabilizing molecule could not provide sufficient stability in order to maintain the polymerase activity (data not shown). Consequently, the combination of a first stabilizing molecule with an aptamer enables the drying and storing of the Taq DNA polymerase in a mixture comprising buffer, nucleotides and primers.

In a preferred method according to the present invention, the aptamer is an aptamer having the sequence SEQ ID NO:9 or SEQ ID NO:10.

Without being bound to theory, it is expected that the aptamers due to their ability to attach to the Taq DNA polymerase enhances the resistance of the polymerase with respect to high salt concentration, extreme pH values and the hydroxyl groups of primers.

In another preferred method according to the present invention, the liquid mixture of reaction compounds is a buffered aqueous solution comprising a magnesium salt.

In a more preferred method according to the present invention, the liquid mixture of reaction compounds is buffered by Tris or Hepes.

In another more preferred method according to the present invention, the liquid mixture of reaction compounds further comprises potassium cloride.

With respect to the drying procedure in step b) of the method according to the present invention, several workflows are suitable. In general, the person skilled in the art will appreciate that the time necessary to dry the liquid mixture will correlate with the pressure surrounding the liquid mixture. Within the present invention it was approved that the pressure should not be lowered to very small pressure values, at least not in one step. If the pressure difference is too large, the liquid mixture will loose contact with the vessel containing the mixture, such that a complete re-solubilization can no longer be realized.

In a preferred method according to the present invention, the pressure surrounding the liquid mixture is reduced in step b) to below 600 mbar, preferably to below 400 mbar, most preferably to 200 mbar.

In a more preferred method according to the present invention, the reduced pressure is maintained for at least 6 hour, preferably for at least 10 hours, most preferably for 16 hours.

Based on suitability for laboratory practice, it is preferred to store the liquid mixture at 200 mbar over night.

In order to reduce the time required to produce the dry composition it is possible to perform the drying step b) of the method according to the present invention in two steps, namely a first step with a relatively high pressure followed by a second step with a lower pressure.

In another preferred method according to the present invention, the pressure is further reduced in a second part of step b), the further reduced pressure is below 200 mbar, preferably below 100 mbar, most preferably is 50 mbar.

In yet another preferred method according to the present invention, the further reduced pressure is maintained for at least 1 hour, preferably for at least 3 hours, most preferably for 4 hours.

A preferred 2-step drying workflow comprises a first step at 200 mbar for 10 hours followed by a second step at 50 mbar for 4 hours.

In still another preferred method according to the present invention, the drying in step b) is performed at room temperature.

Within the present invention it turned out that adjusting the temperature to certain high or low values does not influence the PCR activity upon re-solubilization. Consequently, it is preferred to perform the drying at room temperature.

In order to provide a complete dry composition for real-time PCR, it is necessary to add also detection probes to the liquid mixture of reaction compounds. Within the present invention it was approved that the addition of detection probes to the liquid mixture of reaction compounds does not influence the PCR activity upon re-solubilization. Please note that the Taq DNA polymerase maintained its PCR activity upon re-solubilization even without the aptamer, if the liquid mixture comprises detection probes, but no primers (data not shown).

In a preferred method according to the present invention, the liquid mixture of reaction compounds further comprises detection probes.

In a more preferred method according to the present invention, the detection probes are fluorescence labeled probes, preferably hybridization probes or hydrolysis probes.

Since real-time PCR is generally performed based on fluorescence detection, it is preferred to use fluorescence labeled probes. The main three probe formats are introduced briefly in the following.

a) Hydrolysis Probe Format (TaqMan Format):

A single-stranded Hybridization Probe is labeled with two components. When the first component is excited with light of a suitable wavelength, the absorbed energy is transferred to the second component, the so-called quencher, according to the principle of fluorescence resonance energy transfer. During the annealing step of the PCR reaction, the hybridization probe binds to the target DNA and is degraded by the 5'-3' exonuclease activity of the Taq Polymerase during the subsequent elongation phase. As a result the excited fluorescent component and the quencher are spatially separated from one another and thus a fluorescence emission of the first component can be measured (U.S. Pat. Nos. 5,210,015 , 5,538,848 , 5,487,972, 5,804,375).

b) Molecular Beacons:

These hybridization probes are also labeled with a first component and with a quencher, the labels preferably being located at both ends of the probe. As a result of the secondary structure of the probe, both components are in spatial vicinity in solution. After hybridization to the target nucleic acids both components are separated from one another such that after excitation with light of a suitable wavelength the fluorescence emission of the first component can be measured (U.S. Pat. No. 5,118,801).

c) FRET Hybridization Probes:

This format is characterized by two single-stranded hybridization probes which are used simultaneously and are complementary to adjacent sites of the same strand of the amplified target nucleic acid. Both probes are labeled with different fluorescent components. When excited with light of a suitable wavelength, a first component transfers the absorbed energy to the second component according to the principle of fluorescence resonance energy transfer such that a fluorescence emission of the second component can be measured when both hybridization probes bind to adjacent positions of the target molecule to be detected. Alternatively to monitoring the increase in fluorescence of the FRET acceptor component, it is also possible to monitor fluorescence decrease of the FRET donor component as a quantitative measurement of hybridization event (WO 97/46707; WO 97/46712; WO 97/46714).

In most PCR applications it is desirable to incorporate a control mechanism in order to evaluate, if the PCR amplification as such did work. In general, this is performed with a template DNA spiked to the sample (internal control) or with template DNA within a separate vessel (external control). Throughout the present invention both alternatives are summarized by the phrase positive control.

In a preferred method according to the present invention, the liquid mixture of reaction compounds further comprises template DNA.

In a more preferred method according to the present invention, the template DNA is used as a positive control.

As mentioned before, the experiments within the present invention suggest that the hydroxyl groups at the 3' end of nucleic acids influence the Taq DNA polymerase. Consequently, also template DNA added to the liquid mixture may have a negative impact on the PCR performance after re-solubilization. But probably based on the much lower concentration of template DNA in comparison with normal primer concentrations, it was identified that adding template DNA to the liquid mixture does not influence the PCR performance after re-solubilization.

In a more preferred method according to the present invention, the template DNA is a circular plasmid.

Such a circular plasmid does not have any 3' hydroxyl groups and therefore, the negative impact of hydroxyl groups can be reduced even further.

Another aspect of the present invention is a dry composition of reaction compounds comprising primers, nucleotides, a Taq DNA polymerase, a first stabilizing molecule and an aptamer as a second stabilizing molecule, the dry composition provides PCR activity upon re-solubilization after storage at room temperature for at least one week.

In a more preferred dry composition of reaction compounds according to the present invention, the PCR activity is provided upon re-solubilization after storage at room temperature for at least four weeks, more preferably for at least eight weeks.

Several experiments to evaluate the long term stability were performed and e.g. a dry composition of reaction compounds comprising a Taq DNA polymerase with the aptamer NTQ12-46A (SEQ ID NO:9) as well as primers and probes provided PCR activity upon re-solubilization after storage at room temperature for eight weeks (data not shown).

A preferred dry composition of reaction compounds according to the present invention is a dry composition further comprising detection probes.

In a more preferred dry composition of reaction compounds according to the present invention, the detection probes are fluorescence labeled probes, preferably hybridization probes or hydrolysis probes.

Another preferred dry composition of reaction compounds according to the present invention is dry composition, wherein the first stabilizing molecule is a protein, preferably the stabilizing molecule is casein or BSA.

Yet another preferred dry composition of reaction compounds according to the present invention is dry composition, wherein the first stabilizing molecule is a carbohydrate, preferably the stabilizing molecule is trehalose or mannitol.

Still another preferred dry composition of reaction compounds according to the present invention is dry composition, wherein the first stabilizing molecule is a synthetic polymer, preferably the stabilizing molecule is PEG or polyvinyl pyrrolidone (PVP).

In another preferred dry composition of reaction compounds according to the present invention, the aptamer is an aptamer having the sequence SEQ ID NO:9 or SEQ ID NO:10.

In yet another preferred dry composition of reaction compounds according to the present invention, the liquid mixture of reaction compounds further comprises template DNA.

In a more preferred dry composition of reaction compounds according to the present invention, the template DNA is a positive control.

In another more preferred dry composition of reaction compounds according to the present invention, the template DNA is a circular plasmid.

Yet another aspect of the present invention is a method to perform a PCR amplification, the method comprises the steps
  (a) re-solubilizing a dry composition of reaction compounds according to the present invention by addition of an aqueous solution, and
  (b) performing a thermocycling protocol with the aqueous solution comprising the re-solubilized reaction compounds.

The dry composition of reaction compounds of the present invention can be re-solubilized without special auxiliary means by simply adding aqueous solution. But in order to support the solubilization and reduce the solubilization time it may be preferred to apply mechanical stimulation.

In a preferred method to perform a PCR amplification according to the present invention, the re-solubilization in step b) is supported by shaking of the mixture.

In another preferred method to perform a PCR amplification according to the present invention, the re-solubilization in step b) is supported by vortexing the mixture.

Because only water needs to be added to the dry composition of reaction compounds, two alternatives to perform a PCR amplification are within the scope of the present invention. In the first alternative, the dry composition is re-solubilized with aqueous solution and the sample comprising the target nucleic acid to be analyzed is added afterwards. In the second, preferred alternative, the dry composition is directly re-solubilized with an aqueous solution comprising the target nucleic acid to be amplified.

In a preferred method according to the present invention, the aqueous solution comprises a target nucleic acid to be amplified by the thermocycling protocol.

The following examples, sequence listing and figures are provided to aid the understanding of the present invention, the true scope of which is set forth in the appended claims. It is understood that modifications can be made in the procedures set forth without departing from the spirit of the invention.

EXAMPLE 1

Stability of Taq DNA Polymerase

This example summarizes the results of liquid mixtures of the Taq DNA polymerase without aptamers. The PCR performance of the polymerase after storage and re-solubilization was analyzed with and without detection mix (with or without primers and probes) using two different parameters. The liquid mixtures were dried for 16 h at 200 mbar and stored for 1 week at 37° C. prior to re-solubilization. As a control a liquid mixture without drying was used, too (called liquid reference in the following).

All mixtures were provided within wells of a 384 microtiter plate (Roche Diagnostic GmbH) and after the re-solubilization a PCR run was performed on the LightCycler®480 (Roche Diagnostic GmbH) using the following run protocol:
- 5 minutes 95° C.
- 10 seconds 95° C., 30 seconds 60° C., 1 second 72° C. (45×)
- 10 seconds 40° C.

Mastermix with Casein:
60 mM Tris/HCl pH 8.3, 60 mM KCl, 6.4 mM MgCl2, 0.4 mM dATP, 0.4 mM dCTP, 0.4 mM dGTP, 1.2 mM dUTP, 1 mg/mL casein and 0.3 U/µl Taq DNA Polymerase (glycerol free).

Mastermix with BSA:
60 mM Tris/HCl pH 8.3, 60 mM KCl, 6.4 mM MgCl2, 0.4 mM dATP, 0.4 mM dCTP, 0.4 mM dGTP, 1.2 mM dUTP, 1 mg/ml BSA and 0.3 U/µl Taq DNA Polymerase (glycerol free).

qPCR Eamst Detection Mix:
10 mM Tris pH 8.3, 0.05% Brij, 7.1 µM forward Primer (SEQ ID NO:1), 7.1 µM reverse Primer (SEQ ID NO:2) and 06 µM Fam-Tamra Probe (SEQ ID NO:3).

qPCR Wsebi Detection Mix:
10 mM Tris pH 8.3, 0.05% Brij, 7.1 µM forward Primer (SEQ ID NO:4), 7.1 µM reverse Primer (SEQ ID NO:5) and 0.6 µM Fam-Tamra Probe (SEQ ID NO:6).

The following mixtures were prepared and dried on a microtiter plate, whereas each mixture was placed on the microtiter plate three times:

| | Taq DNA Polymerase | | | |
| --- | --- | --- | --- | --- |
| | Eamst | | Wsebi | |
| | Casein | BSA | Casein | BSA |
| without Detection Mix | 5 µl Master | | 5 µl Master | |
| with Detection Mix | 5 µl Master + 1.4 µl Detection Mix Eamst | | 5 µl Master + 1.4 µl Detection Mix Wsebi | |

For the subsequent PCR amplification the dry compositions were re-solubilized by adding solutions according to the following pipetting scheme. The liquid reference was pipetted prior to the PCR run in empty wells of the microtiter plate. The plasmids were pipetted with a concentration of 4×10e4 copies/µl.

| | Eamst | | | Wsebi | | |
| --- | --- | --- | --- | --- | --- | --- |
| | without Detection Mix | with Detection Mix | liquid reference | without Detection Mix | with Detection Mix | liquid reference |
| water | 6.1 µl | 7.5 µl | 1.1 µl | 6.1 µl | 7.5 µl | 1.1 µl |
| Master Mix | — | — | 5 µl | — | — | 5 µl |
| Eamst Detection Mix | 1.4 µl | — | 1.4 µl | — | — | — |
| Wsebi Detection Mix | — | — | — | 1.4 µl | — | 1.4 µl |
| Eamst Plasmid (SEQ ID NO: 7) | 2.5 µl | 2.5 µl | 2.5 µl | — | — | — |
| Wsebi Plasmid (SEQ ID NO: 8) | — | — | — | 2.5 µl | 2.5 µl | 2.5 µl |
| final volume | 10 µl | 10 µl | 10 µl | 10 µl | 10 µl | 10 µl |

Results:

The PCR amplification curves of this example are summarized in FIGS. 1-4, wherein the curves without detection mix are labeled with "1", the curves with detection mix are labeled with "2" and the curves of the liquid reference are labeled with "3". Moreover, the following table summarizes the PCR values obtained from the curves of FIGS. 1-4.

| | | Taq DNA Polymerase | | | | | |
| --- | --- | --- | --- | --- | --- | --- | --- |
| | | Eamst | | | Wsebi | | |
| | | without Detection Mix | with Detection Mix | liquid reference | without Detection Mix | with Detection Mix | liquid reference |
| Casein | Crossing Point | 24.7 | 21.1 | 24.8 | 26.2 | — | 26.6 |
| | fluorescence | 7.2 | 2.0 | 7.2 | 5.7 | — | 5.8 |
| BSA | Crossing Point | 24.5 | 21.7 | 24.8 | 25.9 | — | 26.6 |
| | fluorescence | 7.5 | 1.8 | 8.0 | 5.5 | — | 7.0 |

From this example it is clear that the performance of the Taq DNA Polymerase dried without the detection mix is identical to that of the Taq DNA Polymerase within the liquid reference. On the other hand, if the Taq DNA Polymerase is dried with the detection mix, the PCR performance after re-solubilization is no longer acceptable.

With respect to the Wsebi parameter, no amplification is detectable at all in case of drying with detection mix. With respect to the Eamst parameter, a similar crossing point is still detectable, but the fluorescence value is no longer acceptable.

EXAMPLE 2

Stability of Taq DNA Polymerase with Aptamer NTQ12-46A

This example summarizes the results of liquid mixtures of the Taq DNA polymerase with the aptamer NTQ12-46A (SEQ ID NO:9). A Taq DNA polymerase with attached aptamer is named AptaTaq DNA polymerase NTQ12-46A throughout this example.

The PCR performance of the polymerase after storage and re-solubilization was analyzed with and without detection mix (with or without primers and probes) using two different parameters. The liquid mixtures were dried 16 hours at 200 mbar and stored for 1 week at 37° C. prior to re-solubilization. As a control a liquid mixture without drying was used, too (called liquid reference in the following).

All mixtures were provided within wells of a 384 microtiter plate (Roche Diagnostic GmbH) and after the re-solubilization a PCR run was performed on the LightCycler®480 (Roche Diagnostic GmbH) using the following run protocol:
- 5 minutes 95° C.
- 10 seconds 95° C., 30 seconds 60° C., 1 second 72° C. (45×)
- 10 seconds 40° C.

Mastermix with Casein:
60 mM Tris/HCl pH 8.3, 60 mM KCl, 6.4 mM MgCl2, 0.4 mM dATP, 0.4 mM dCTP, 0.4 mM dGTP, 1.2 mM dUTP, 1 g/L casein and 0.3 U/µl AptaTaq DNA Polymerase (glycerol free; 0.65 pmol Aptamer (NTQ12-46A; SEQ ID NO:9)/1U Taq DNA Polymerase).

Mastermix with BSA:
60 mM Tris/HCl pH 8.3, 60 mM KCl, 6.4 mM MgCl2, 0.4 mM dATP, 0.4 mM dCTP, 0.4 mM dGTP, 12 mM dUTP, 1 mg/ml BSA and 03 U/µl AptaTaq DNA Polymerase (glycerol free; 065 pmol Aptamer (NTQ12-46A; SEQ ID NO:9)/1U Taq DNA Polymerase).

qPCR Eamst Detection Mix and qPCR Wsebi Detection Mix:
These detection mixtures are the same like in example 1.

The following mixtures were prepared and dried on a microtiter plate, whereas each mixture was placed on the microtiter plate three times:

|  | AptaTaq DNA Polymerase NTQ12-46A | | | |
| --- | --- | --- | --- | --- |
|  | Eamst | | Wsebi | |
|  | Casein | BSA | Casein | BSA |
| without Detection Mix | 5 µl Master | | 5 µl Master | |
| with Detection Mix | 5 µl Master + 1.4 µl Detection Mix Eamst | | 5 µl Master + 1.4 µl Detection Mix Wsebi | |

For the subsequent PCR amplification the dry compositions were re-solubilized by adding solutions according to the following pipetting scheme. The liquid reference was pipetted prior to the PCR run in empty wells of the microtiter plate. The plasmids were pipetted with a concentration of 4×10e4 copies/µl.

|  | Eamst | | | Wsebi | | |
| --- | --- | --- | --- | --- | --- | --- |
|  | without Detection Mix | with Detection Mix | liquid reference | without Detection Mix | with Detection Mix | liquid reference |
| water | 6.1 µl | 7.5 µl | 1.1 µl | 6.1 µl | 7.5 µl | 1.1 µl |
| Master Mix | — | — | 5 µl | — | — | 5 µl |
| Eamst Detection Mix | 1.4 µl | — | 1.4 µl | — | — | — |
| Wsebi Detection Mix | — | — | — | 1.4 µl | — | 1.4 µl |
| Eamst Plasmid (SEQ ID NO: 7) | 2.5 µl | 2.5 µl | 2.5 µl | — | — | — |
| Wsebi Plasmid (SEQ ID NO: 8) | — | — | — | 2.5 µl | 2.5 µl | 2.5 µl |
| final volume | 10 µl | 10 µl | 10 µl | 10 µl | 10 µl | 10 µl |

Results:

The PCR amplification curves of this example are summarized in FIGS. 5-8, wherein the curves after drying without detection mix are labeled with "1", the curves after drying with detection mix are labeled with "2" and the curves of the liquid reference (without drying) are labeled with "3". Moreover, the following table summarizes the PCR values obtained from the curves of FIGS. 5-8.

| | | AptaTaq DNA Polymerase NTQ12-46A | | | | |
|---|---|---|---|---|---|---|
| | | Eamst | | | Wsebi | |
| | | without Detection Mix | with Detection Mix | liquid reference | without Detection Mix | with Detection Mix | liquid reference |
| Casein | Crossing Point | 24.3 | 23.9 | 24.9 | 24.1 | 24.0 | 25.1 |
| | fluorescence | 6.7 | 5.7 | 7.3 | 4.3 | 4.1 | 5.4 |
| BSA | Crossing Point | 24.6 | 24.2 | 25.0 | 24.4 | 24.2 | 25.0 |
| | fluorescence | 6.5 | 5.3 | 7.6 | 4.3 | 4.0 | 6.0 |

Figure 2:
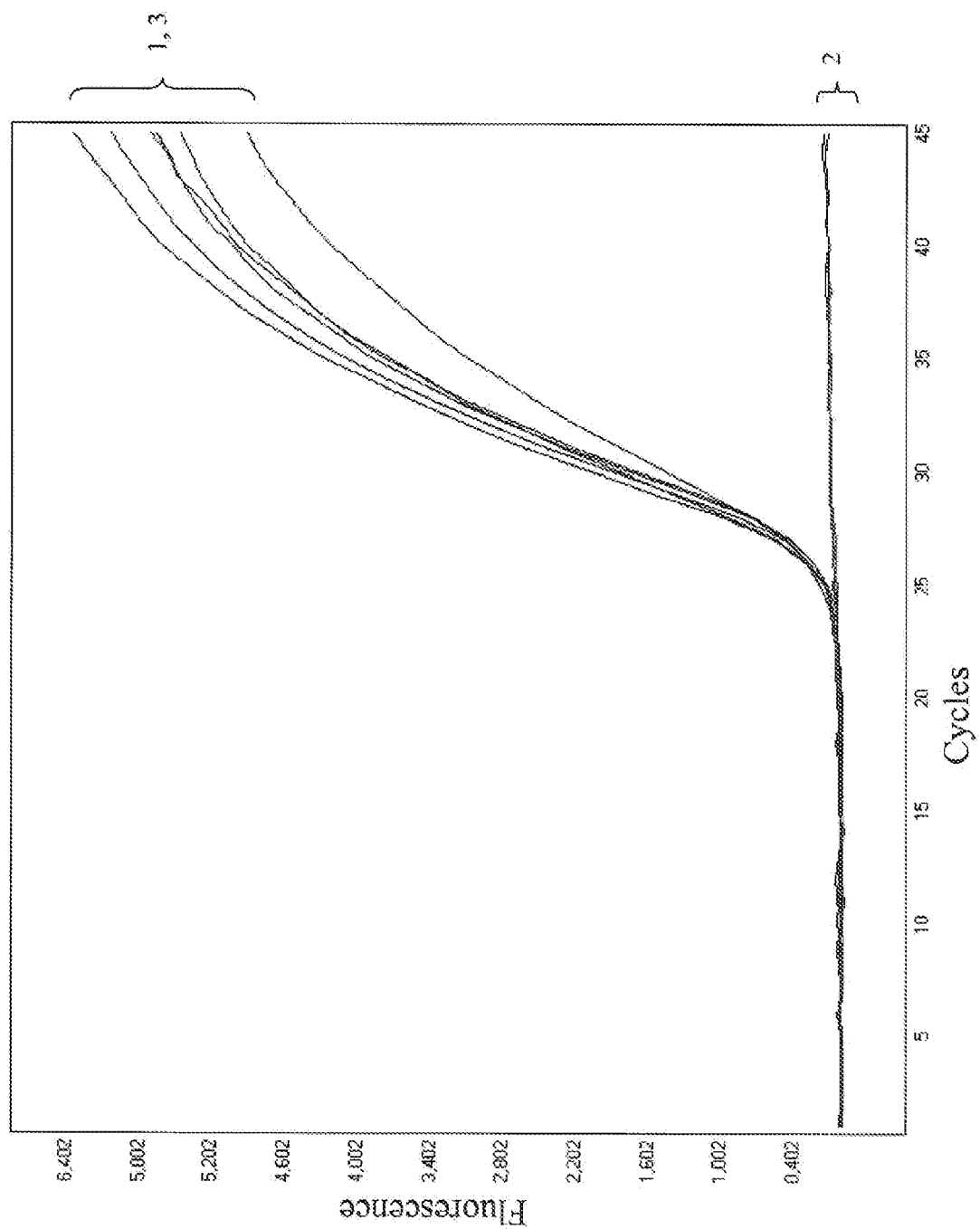
Figure 3:
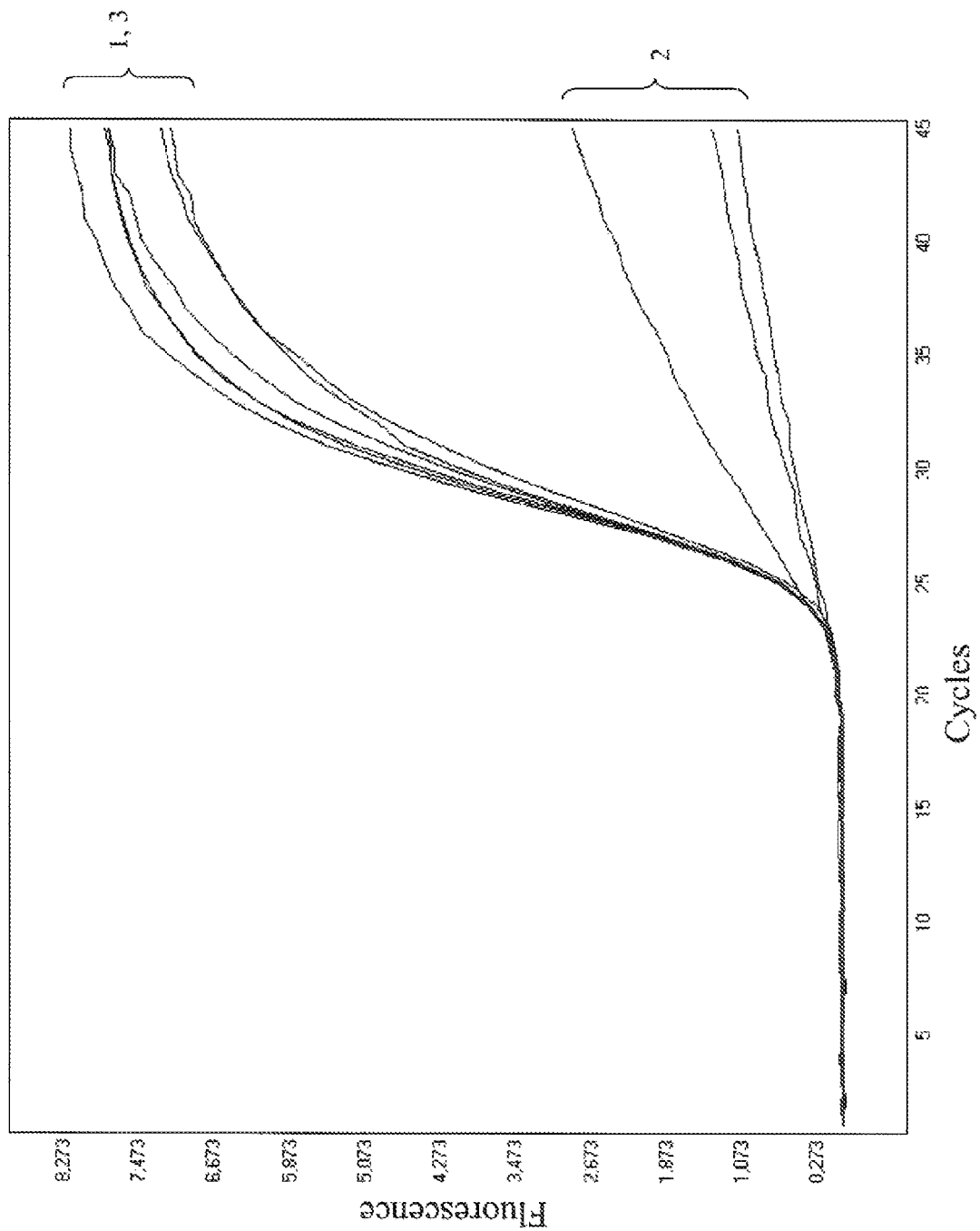
Figure 4:
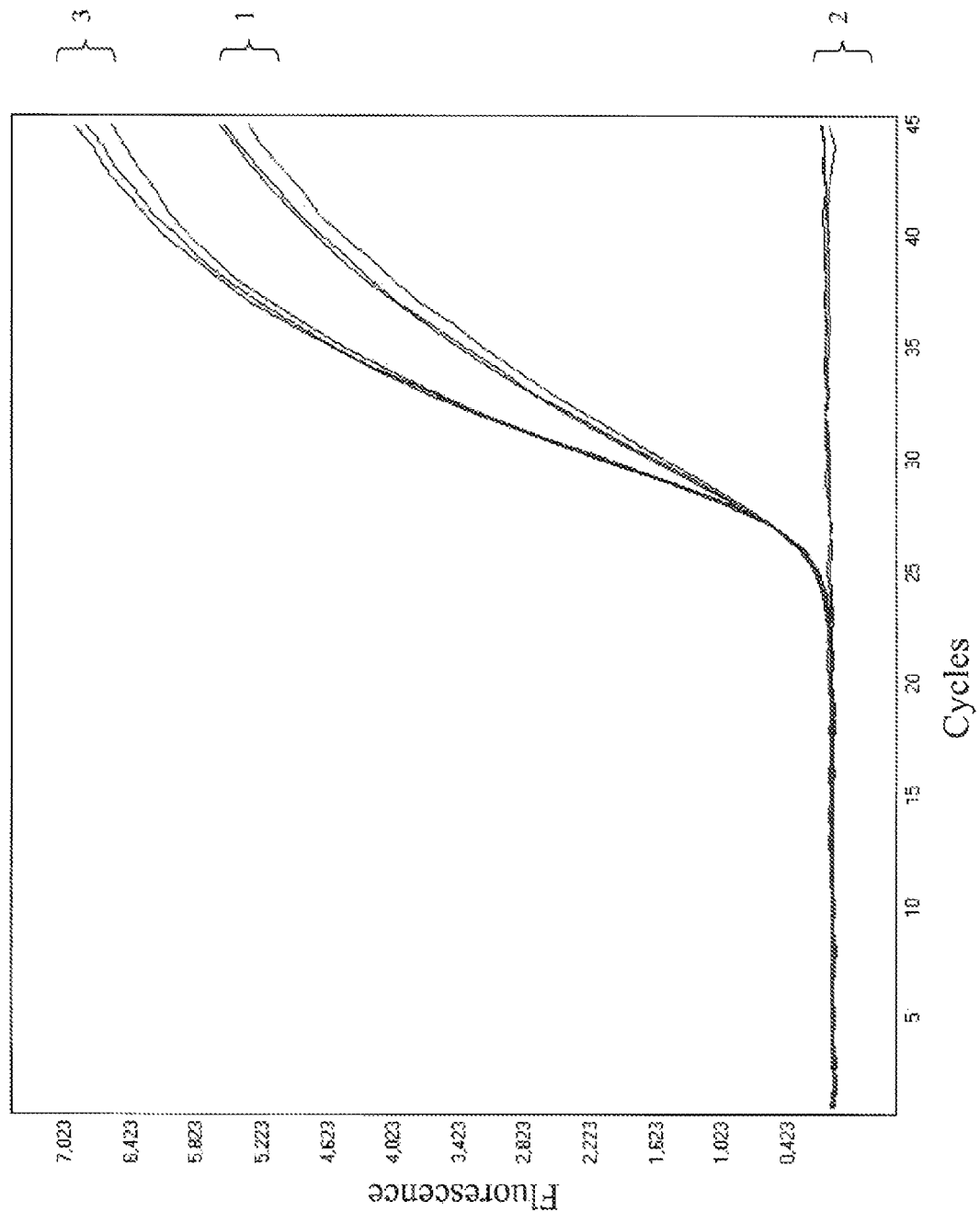
Figure 5:
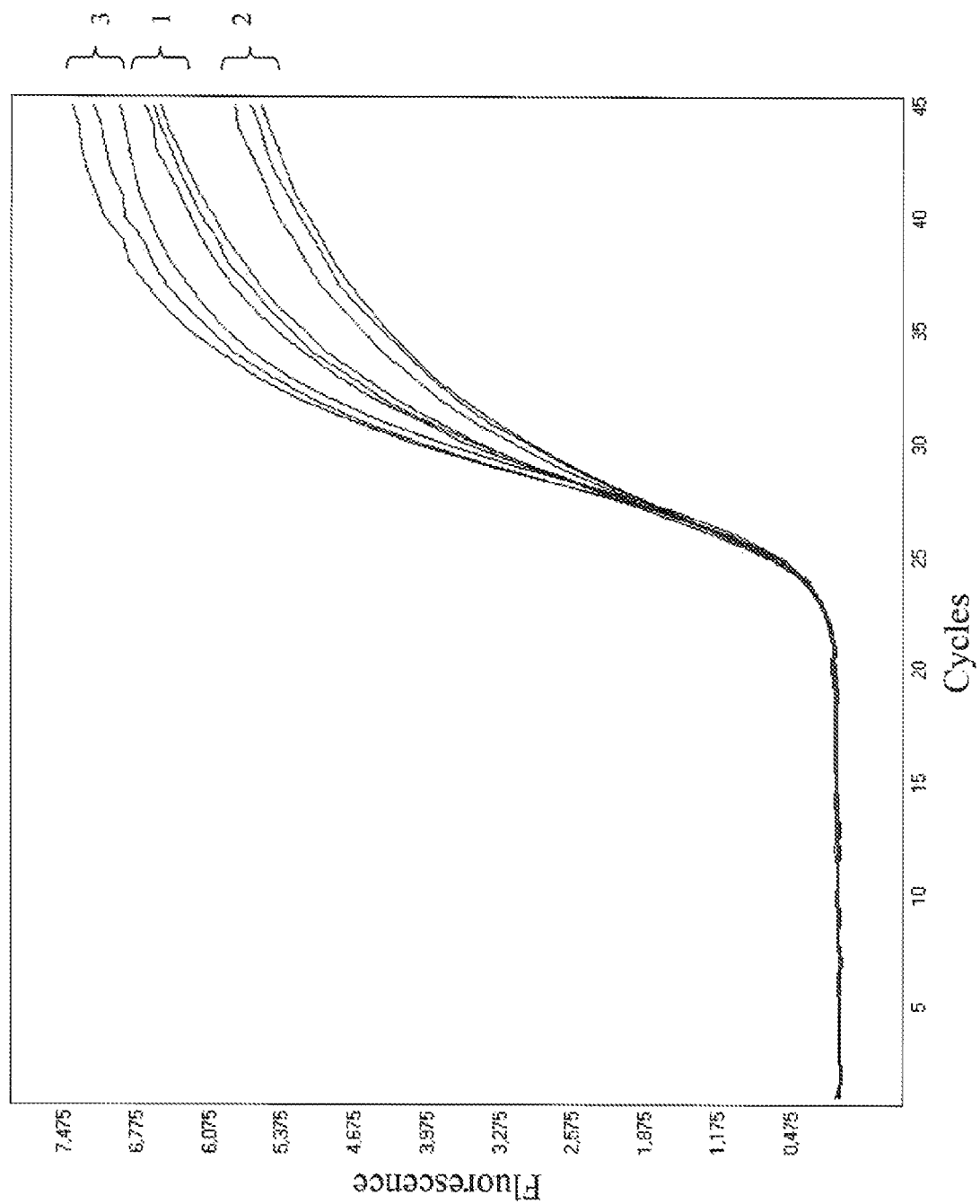
Figure 6:
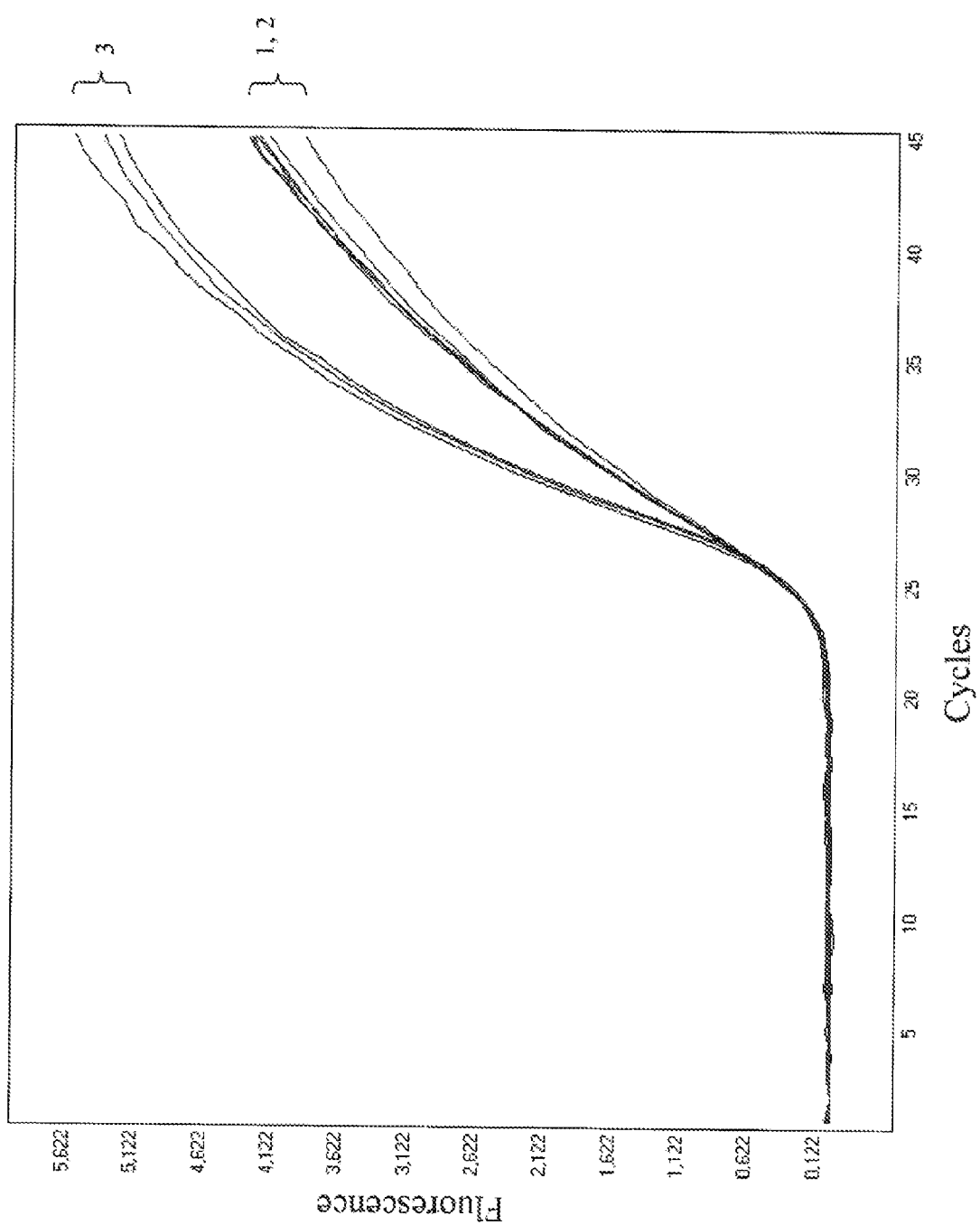
Figure 7:
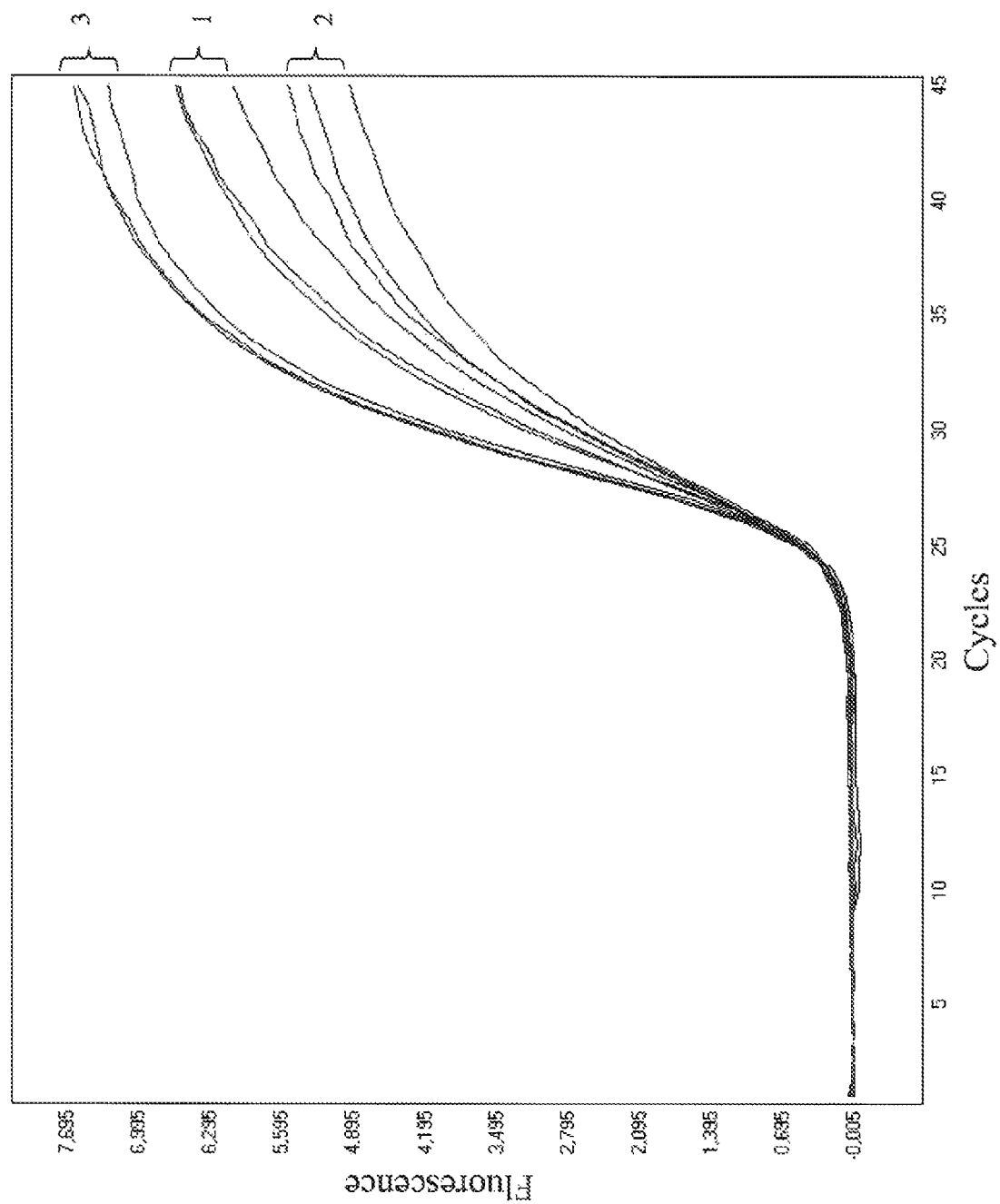
Figure 8:
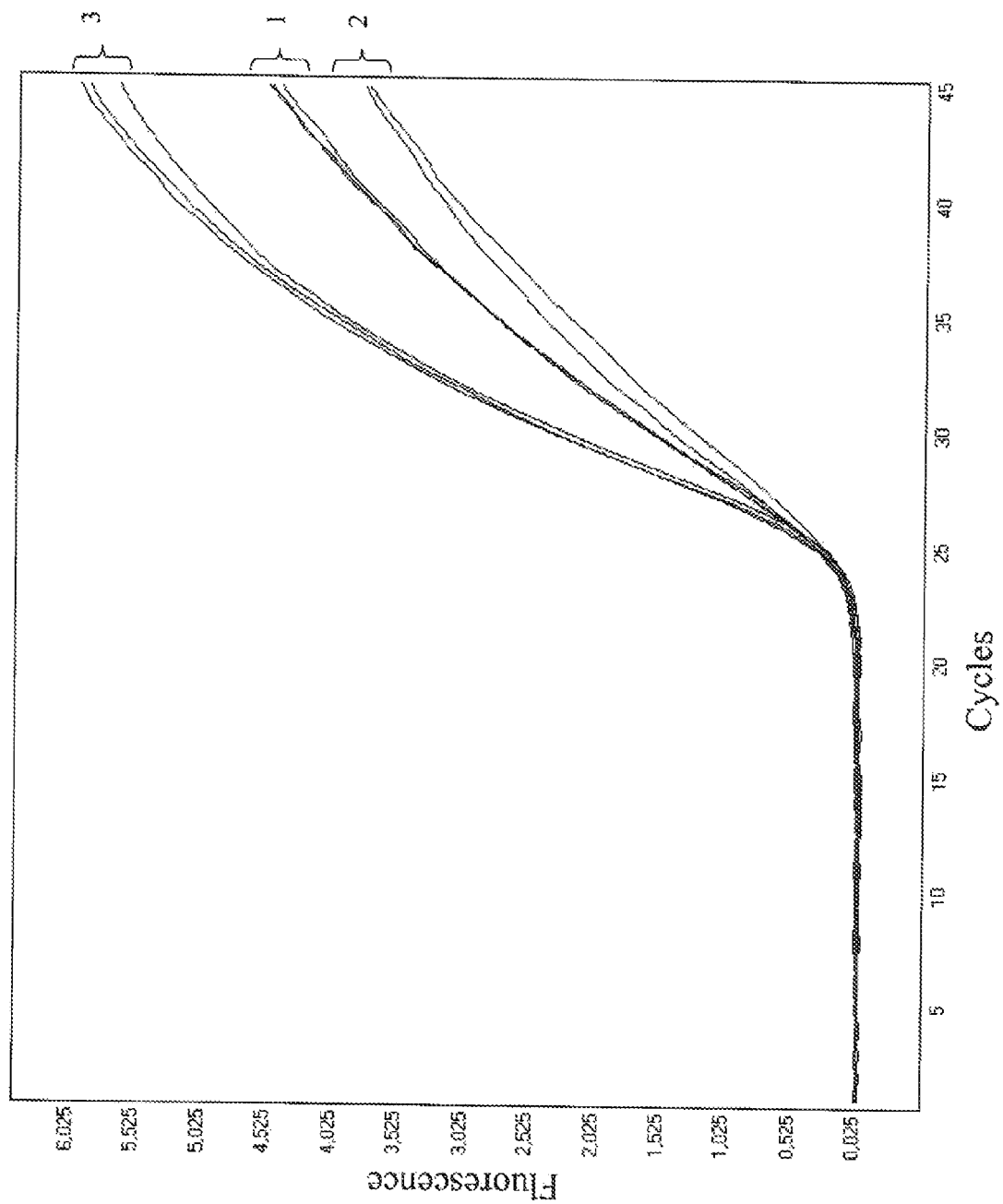
Figure 9:
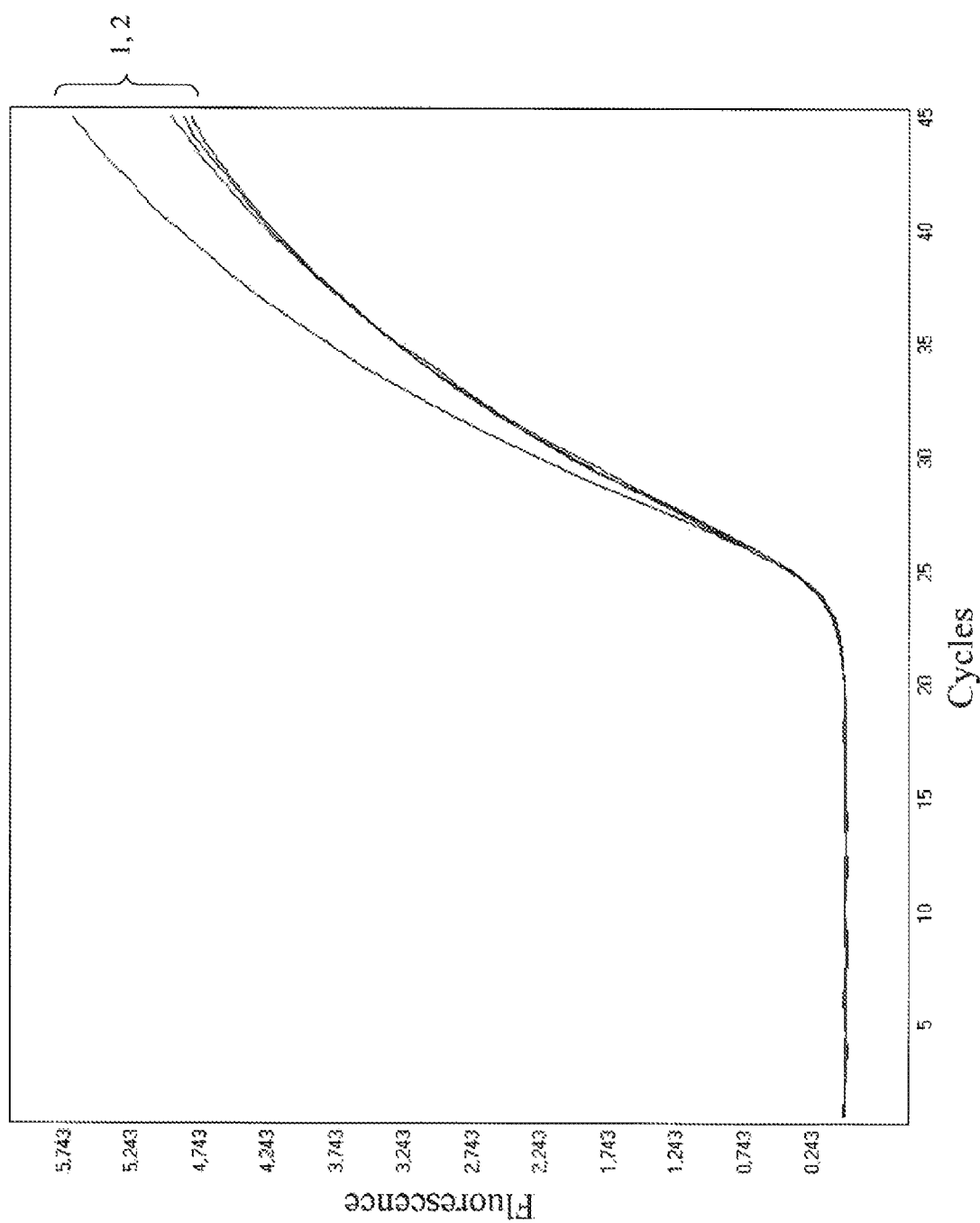
Figure 10:
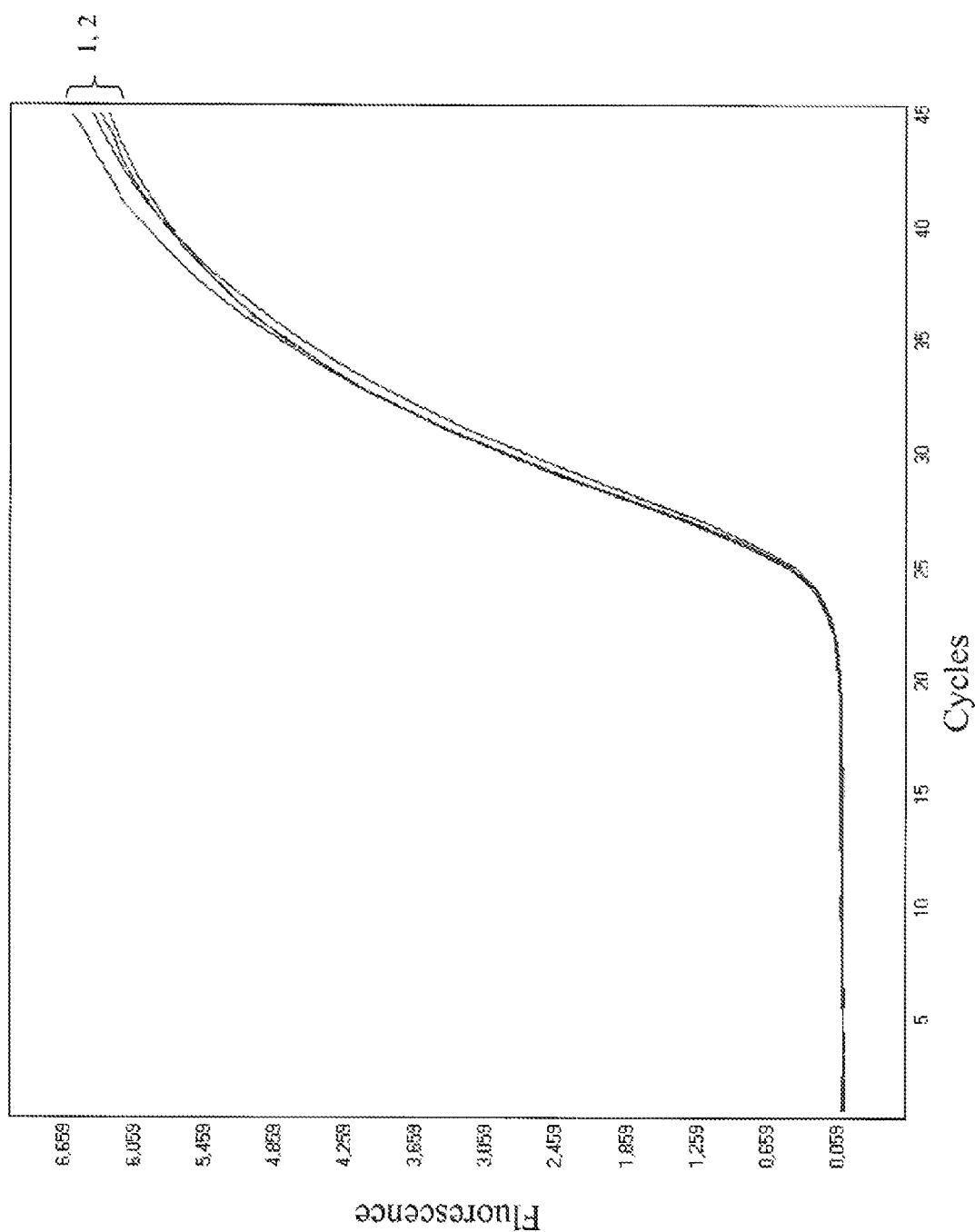
Figure 11:
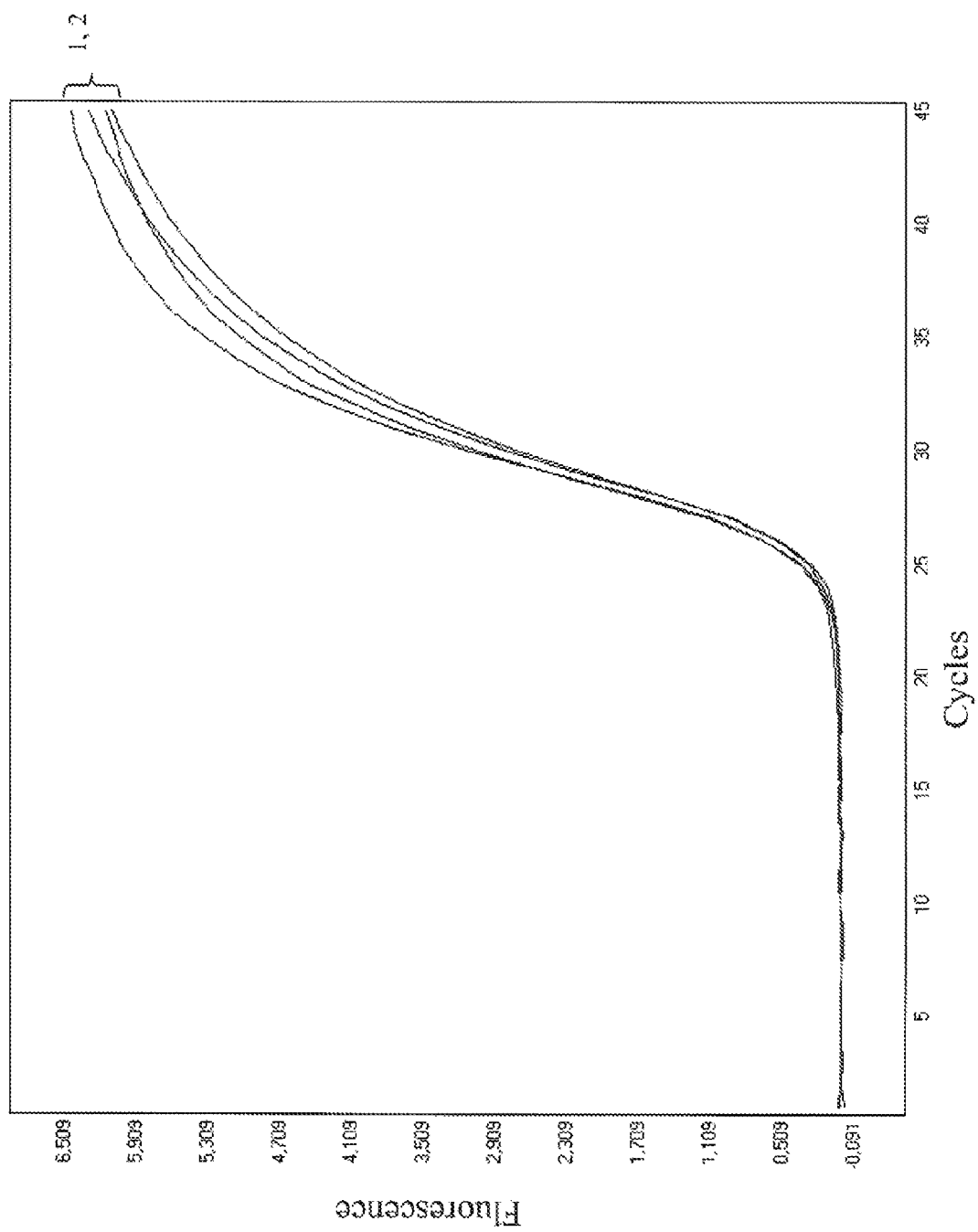
Figure 12:
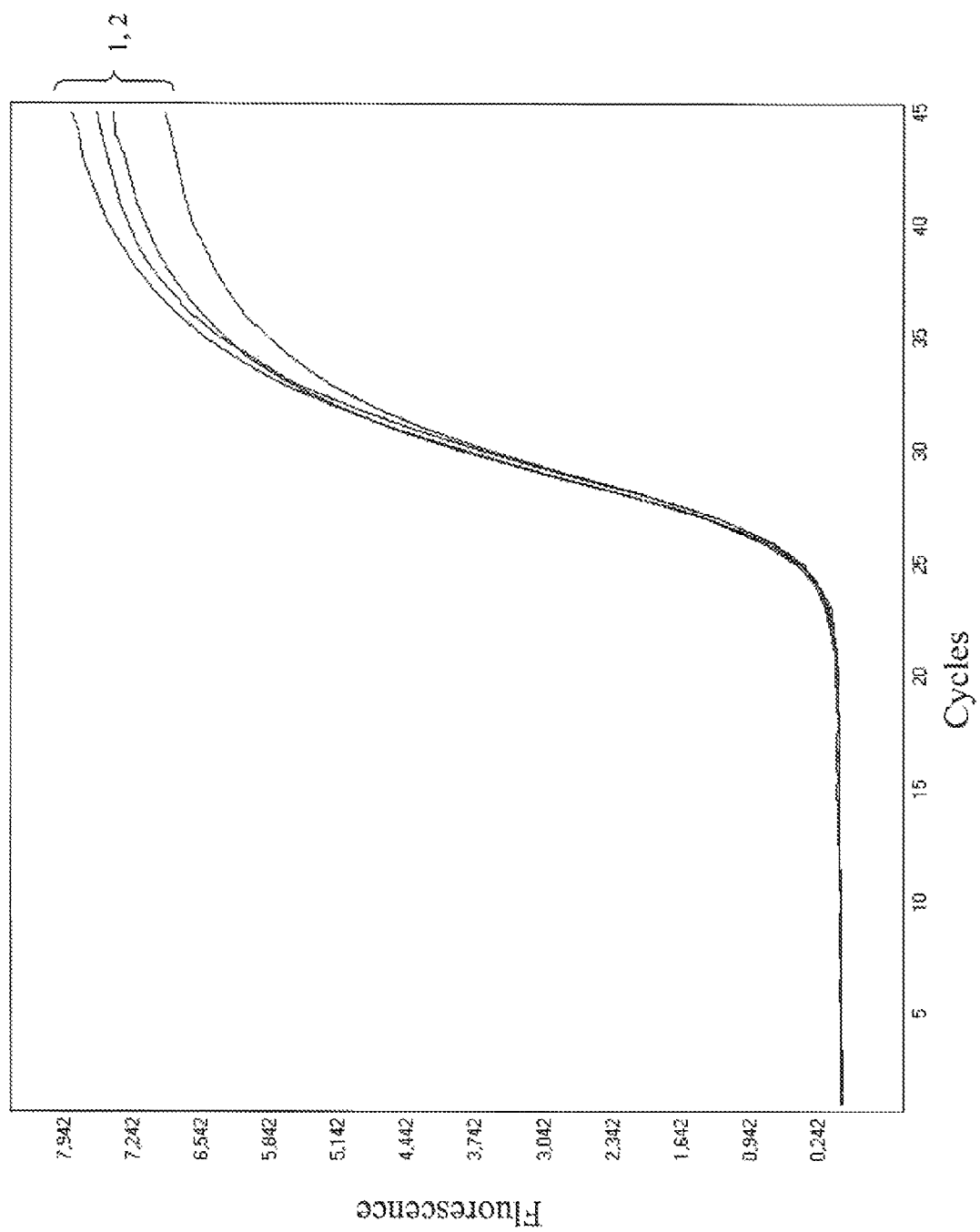

In order to verify the stabilizing properties of the aptamer the amplification curves of FIGS. 5-8 needs to be compared with FIGS. 1-4, more precisely FIG. 5 with FIG. 1, FIG. 6 with FIG. 2, FIG. 7 with FIG. 3, FIG. 8 with FIG. 4. It is clear that FIGS. 1-4 show drastically reduced amplification curves after drying, whereas the FIGS. 5-8 show only slightly altered curves after drying.

From this example it is clear that the performance of the AptaTaq DNA Polymerase NTQ12-46A dried with or without the detection mix is still acceptable after the re-solubilization of the dry composition.

EXAMPLE 3

Comparison of Taq DNA Polymerase with Aptamer NTQ12-46A and with Aptamer 21-42-P Within this example the PCR performance of liquid mixtures of the Taq DNA polymerase with the aptamer NTQ12-46A (SEQ ID NO:9) is compared with the aptamer 21-42-P (SEQ ID NO:10). A Taq DNA polymerases with attached aptamer are named AptaTaq DNA polymerase NTQ12-46A and AptaTaq DNA polymerase 21-42-P throughout this example, respectively.

The PCR performance of the polymerase with both aptamers were analyzed with detection mix (with primers and probes) after storage and re-solubilization using two different parameters. The liquid mixtures were dried 16 hours at 200 mbar and stored for 1 week at 37° C. prior to re-solubilization. As a control a liquid mixture without drying was used, too (called liquid reference in the following).

All mixtures were provided within wells of a 384 microtiter plate (Roche Diagnostic GmbH) and after the re-solubilization a PCR run was performed on the LightCycler®480 (Roche Diagnostic GmbH) using the following run protocol:
 –5 minutes 95° C.
 –10 seconds 95° C., 30 seconds 60° C., 1 second 72° C. (45×)
 –10 seconds 40° C.
Mastermix with Casein+Aptamer NTQ21-46A:
 60 mM Tris/HCl pH 8.3, 60 mM KCl, 6.4 mM MgCl2, 0.4 mM dATP, 0.4 mM dCTP, 04 mM dGTP, 1.2 mM dUTP, 1 WI. Casein and 0.3 U/µl AptaTaq DNA Polymerase (glycerol free; 0.65 pmol Aptamer NTQ12-46A (SEQ ID NO:9)/1 U Taq DNA Polymerase).
Mastermix with Casein+Aptamer 21-42-P:
 60 mM Tris/HCl pH 8.3, 60 mM KCl, 6.4 mM MgCl2, 0.4 mM dATP, 0.4 mM dCTP, 0.4 mM dGTP, 1.2 mM dUTP, 1 g/L casein, 0.8 U/µl AptaTaq DNA Polymerase (glycerol free; 0.5 µM Aptamer 21-42-P (SEQ ID NO:10).
qPCR Eamst Detection Mix and qPCR Wsebi Detection Mix:
 These detection mixtures are the same like in example 1.

The following mixtures were prepared and dried on a microtiter plate, whereas each mixture was placed on the microtiter plate three times:

| | Taq DNA Polymerase with different Aptamer | | | |
|---|---|---|---|---|
| | Eamst | | Wsebi | |
| | NTQ21-46A | 21-42-P | NTQ21-46A | 21-42-P |
| with Detection Mix | 5 µl Master + 1.4 µl Detection Mix Eamst | | 5 µl Master + 1.4 µl Detection Mix Wsebi | |

For the subsequent PCR amplification the dry compositions for each aptamer were re-solubilized by adding solutions according to the following pipetting scheme. The liquid reference was pipetted prior to the PCR run in empty wells of the microtiter plate. The plasmids were pipetted with a concentration of 4×10e4 copies/µl.

| | Eamst | | Wsebi | |
|---|---|---|---|---|
| | with Detection Mix | liquid reference | with Detection Mix | liquid reference |
| water | 7.5 µl | 1.1 µl | 7.5 µl | 1.1 µl |
| 2x Master Mix | — | 5 µl | — | 5 µl |
| Eamst Detection Mix | — | 1.4 µl | — | — |
| Wsebi Detection Mix | — | — | — | 1.4 µl |
| Eamst Plasmid (SEQ ID NO: 7) | 2.5 µl | 2.5 µl | — | — |
| Wsebi Plasmid (SEQ ID NO: 8) | — | — | 2.5 µl | 2.5 µl |
| final volume | 10 µl | 10 µl | 10 µl | 10 µl |

Results:

The PCR amplification curves of this example are summarized in FIGS. 9-12, wherein the curves after drying with detection mix are labeled with "1" and the curves of the liquid reference (without drying) are labeled with "2". Moreover, the following table summarizes the PCR values obtained from the curves of FIGS. 9-12.

| | | Aptamer NTQ21-46A | | Aptamer 21-42-P | |
|---|---|---|---|---|---|
| | | Eamst | Wsebi | Eamst | Wsebi |
| dried Master with Detection Mix | Crossing Point | 25.5 | 24.1 | 25.5 | 24.8 |
| | fluorescence | 6.4 | 5.0 | 7.3 | 6.4 |

|  | | Aptamer NTQ21-46A | | Aptamer 21-42-P | |
|---|---|---|---|---|---|
|  | | Earnst | Wsebi | Earnst | Wsebi |
| liquid reference | Crossing Point | 25.6 | 24.2 | 25.6 | 24.7 |
|  | fluorescence | 6.3 | 5.3 | 7.8 | 6.6 |

Again, in order to verify the stabilizing properties of the aptamer the amplification curves of FIGS. 9-12 needs to be compared with FIGS. 1-4 and it is clear that FIGS. 1-4 show drastically reduced amplification curves after drying, whereas the FIGS. 9-12 show only slightly altered curves after drying.

From this example it is clear that the performance of the AptaTaq DNA Polymerase NTQ12-46A and of the AptaTaq DNA Polymerase 21-41-P dried with detection mix are comparable after re-solubilization of the dry composition.

EXAMPLE 4

Apta Tag DNA Polymerase NTQ12-46A Dried with Plasmid DNA

Within this example a liquid mixture with AptaTaq DNA Polymerase NTQ12-46A, plasmid DNA of two different parameters and the respective detection mix were dried and the PCR performance after storage and re-solubilization was compared to liquid mixtures without the plasmids. The liquid mixtures were dried 16 hours at 200 mbar and stored for 1 week at 37° C. prior to re-solubilization. As a control a liquid mixture without drying was used, too (called liquid reference in the following). All mixtures were provided within wells of a 384 microtiter plate (Roche Diagnostic GmbH) and after the re-solubilization a PCR run was performed on the LightCycler®480 (Roche Diagnostic GmbH) using the following run protocol:
- –5 minutes 95° C.
- –10 seconds 95° C., 30 seconds 60° C., 1 second 72° C. (45×)
- –10 seconds 40° C.

Master mix and both detection mixtures are the same as in example 2.

The following mixtures were prepared and dried on a microtiter plate, whereas each mixture was placed on the microtiter plate three times. The plasmids were pipetted with a concentration of $4 \times 10e4$ copies/µl.

|  | AptaTaq DNA Polymerase NTQ12-46A | |
|---|---|---|
|  | Earnst | Wsebi |
| Master with Detection Mix | 5 µl Master + 1.4 µl Detection Mix Earnst | 5 µl Master + 1.4 µl Detection Mix Wsebi |
| Master with Detection Mix and with Plasmid DNA | 5 µl Master + 1.4 µl Detection Mix Earnst + 2.5 µl Plasmid DNA Earnst | 5 µl 2x Master + 1.4 µl Detection Mix Wsebi + 2.5 µl Plasmid DNA Wsebi |

For the subsequent PCR amplification the dry compositions for each mixture were re-solubilized by adding solutions according to the following pipetting scheme. The liquid reference was pipetted prior to the PCR run in empty wells of the microtiter plate.

|  | Earnst | | | Wsebi | | |
|---|---|---|---|---|---|---|
|  | Master with Detection Mix | Master with Detection Mix and Plasmid | liquid reference | Master with Detection Mix | Master with Detection Mix and Plasmid | liquid reference |
| water | 7.5 µl | 10 µl | 1.1 µl | 7.5 µl | 10 µl | 1.1 µl |
| Master Mix | — | — | 5 µl | — | — | 5 µl |
| Earnst Detection Mix | — | — | 1.4 µl | — | — | — |
| Wsebi Detection Mix | — | — | — | — | — | 1.4 µl |
| Earnst Plasmid | 2.5 µl | — | 2.5 µl | — | — | — |
| Wsebi Plasmid | — | — | — | 2.5 µl | — | 2.5 µl |
| final volume | 10 µl | 10 µl | 10 µl | 10 µl | 10 µl | 10 µl |

Figure 13:
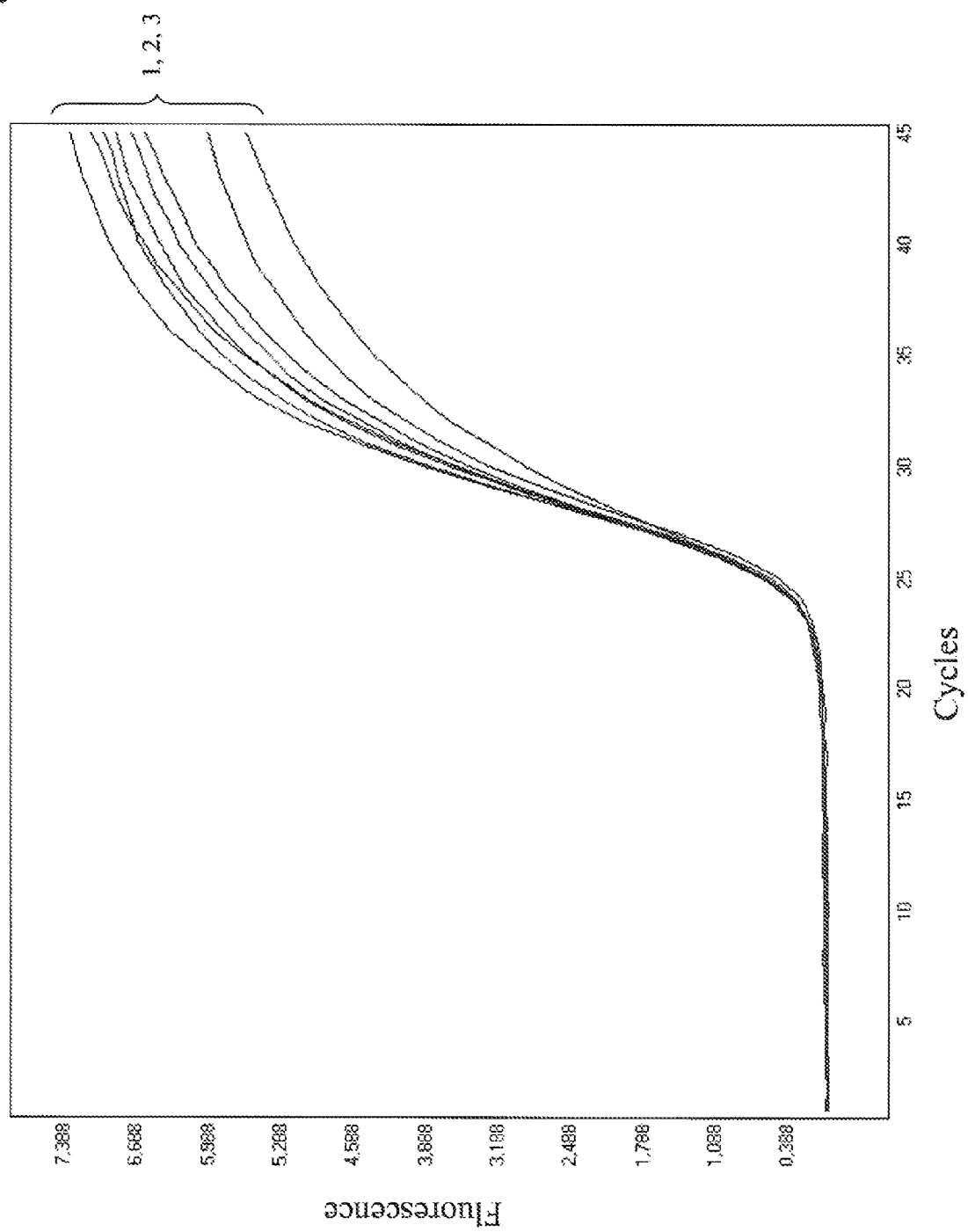
Figure 14:
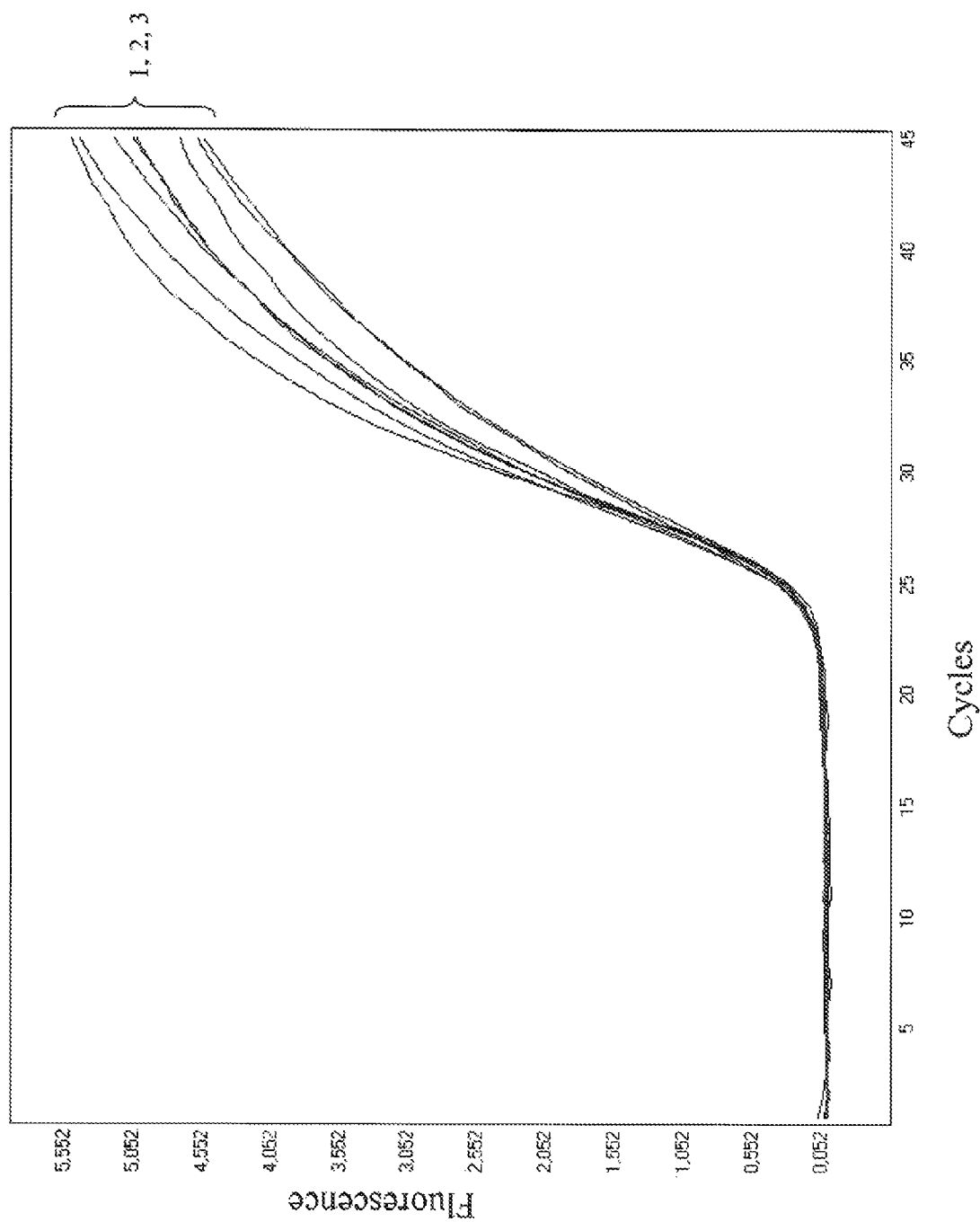

Results:

The PCR amplification curves of this example are summarized in FIGS. 13-14, wherein the curves after drying without plasmid are labeled with "1", the curves after drying with plasmid are labeled with "2" and the curves of the liquid reference (without drying) are labeled with "3". Moreover, the following table summarizes the PCR values obtained from the curves of FIGS. 13-14.

|  |  | Earnst | Wsebi |
|---|---|---|---|
| Master with Detection Mix | Crossing Point | 24.5 | 24.8 |
|  | fluorescence | 6.6 | 5.2 |
| Master with Detection Mix and Plasmid | Crossing Point | 24.5 | 24.5 |
|  | fluorescence | 6.5 | 5.0 |
| liquid reference | Crossing Point | 24.9 | 24.9 |
|  | fluorescence | 7.3 | 5.0 |

From this example it is clear that the performance of the AptaTaq DNA Polymerase NTQ12-46A after storage and re-solubilization of the dry composition is not influenced, if a plasmid is added to the liquid mixture prior to drying.

What is claimed is:

1. A dry composition of reaction compounds comprising primers, nucleotides, a Taq DNA polymerase, a first stabilizing molecule, and an aptamer as a second stabilizing molecule, the dry composition providing polymerase chain reaction (PCR) activity upon re-solubilization after storage at room temperature for at least one week.

2. The dry composition of reaction compounds of claim 1 wherein the composition further comprises detection probes.

3. The dry composition of reaction compounds of claim 1 wherein the first stabilizing molecule is casein or BSA.

4. The dry composition of reaction compounds of claim 1 wherein the aptamer has the sequence of SEQ ID NO: 9 or SEQ ID NO: 10.

* * * * *